United States Patent
Schoonmaker et al.

(10) Patent No.: US 10,258,749 B2
(45) Date of Patent: Apr. 16, 2019

(54) MULTI-STROKE DELIVERY PUMPING MECHANISM FOR A DRUG DELIVERY DEVICE FOR HIGH PRESSURE INJECTIONS

(71) Applicant: Becton, Dickinson and Company, Franklin Lakes, NJ (US)

(72) Inventors: Ryan Schoonmaker, Oceanside, CA (US); Michel Bruehwiler, Newton, MA (US); Ira Spool, Newton, MA (US); Melissa Rosen, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 591 days.

(21) Appl. No.: 14/962,508

(22) Filed: Dec. 8, 2015

(65) Prior Publication Data

US 2016/0158462 A1 Jun. 9, 2016

Related U.S. Application Data

(62) Division of application No. 12/998,840, filed as application No. PCT/US2009/006421 on Dec. 8, 2009, now Pat. No. 9,238,112.
(Continued)

(51) Int. Cl.
*A61M 5/48* (2006.01)
*A61M 5/20* (2006.01)
(Continued)

(52) U.S. Cl.
CPC .......... *A61M 5/48* (2013.01); *A61M 5/14216* (2013.01); *A61M 5/204* (2013.01);
(Continued)

(58) Field of Classification Search
CPC .. A61M 5/19; A61M 5/3155; A61M 5/31551; A61M 5/31553; A61M 5/31555;
(Continued)

(56) References Cited

U.S. PATENT DOCUMENTS 4,231,368 A 11/1980 Beckner
4,465,478 A 8/1984 Sabelman
(Continued)

FOREIGN PATENT DOCUMENTS

JP 2003-509133 A 3/2003
JP 2004-503303 A 2/2004
(Continued)

*Primary Examiner* — Kami A Bosworth
(74) *Attorney, Agent, or Firm* — Dickinson Wright PLLC

(57) ABSTRACT

A dual-chambered drug delivery device, comprising a cartridge having a first chamber for storing a medicament, a second chamber in fluid communication with said first chamber, a dose setting member for setting a medicament dose to be injected at an injection site, a piston disposed in said second chamber, an upward stroke of said piston drawing a portion of the medicament dose into said second chamber and a downward stroke of said piston expelling the portion of the medicament dose, a needle communicating with said second chamber for sequentially injecting portions of the medicament dose into the injection site, a drive screw movably connected to said dose setting member such that rotation of said dose setting member moves said drive screw upwardly, and a rack movably connected to said drive screw such that downward movement of said drive screw during the medicament dose injection rotates said rack.

10 Claims, 28 Drawing Sheets

Related U.S. Application Data

(60) Provisional application No. 61/193,594, filed on Dec. 9, 2008.

(51) Int. Cl.
    *A61M 5/315*     (2006.01)
    *A61M 5/142*     (2006.01)
    *A61M 5/28*     (2006.01)
    *A61M 5/31*     (2006.01)

(52) U.S. Cl.
    CPC .... *A61M 5/31511* (2013.01); *A61M 5/31553* (2013.01); *A61M 5/286* (2013.01); *A61M 5/3146* (2013.01); *A61M 5/3158* (2013.01); *A61M 2005/3128* (2013.01); *A61M 2005/3152* (2013.01); *A61M 2005/31518* (2013.01)

(58) Field of Classification Search
    CPC .......... A61M 5/31556; A61M 5/31558; A61M 5/3156; A61M 5/31561; A61M 5/31563; A61M 5/3158; A61M 5/204; A61M 2005/3152; A61M 2005/31518; A61M 2005/3128; A61M 2005/3114
    See application file for complete search history.

(56) References Cited

U.S. PATENT DOCUMENTS

| | | |
|---|---|---|
| 4,643,723 A | 2/1987 | Smit |
| 4,865,591 A * | 9/1989 | Sams ................ A61M 5/31553 222/287 |
| 5,271,527 A * | 12/1993 | Haber ................ A61M 5/19 222/137 |
| 5,279,585 A | 1/1994 | Balkwill |
| 5,279,586 A | 1/1994 | Balkwill |
| 5,281,198 A * | 1/1994 | Haber ................ A61J 1/2093 604/191 |
| 5,298,023 A * | 3/1994 | Haber ................ A61M 5/2448 604/191 |
| 5,549,575 A | 8/1996 | Giambattista |
| 5,569,214 A | 10/1996 | Chanoch |
| 5,582,598 A | 12/1996 | Chanoch |
| 5,584,815 A * | 12/1996 | Pawelka ................ A61M 5/19 604/135 |
| 5,674,204 A | 10/1997 | Chanoch |
| 5,823,998 A * | 10/1998 | Yamagata ........... A61M 5/2448 604/131 |
| 5,843,042 A | 12/1998 | Ren |
| 5,921,966 A | 7/1999 | Bendek |
| 5,944,700 A | 8/1999 | Nguyen |
| 5,957,896 A | 9/1999 | Bendek |
| 6,096,010 A | 8/2000 | Walters |
| 6,110,149 A | 8/2000 | Klitgaard |
| 6,221,053 B1 | 4/2001 | Walters |
| 6,248,095 B1 | 6/2001 | Giambattista |
| 6,277,099 B1 | 8/2001 | Strowe |
| 6,537,242 B1 | 3/2003 | Palmer |
| 6,582,404 B1 | 6/2003 | Klitgaard |
| 6,692,472 B2 | 2/2004 | Hansen |
| 6,932,794 B2 | 8/2005 | Giambattista |
| 6,936,032 B1 | 8/2005 | Bush, Jr. |
| 6,945,961 B2 | 9/2005 | Miller |
| 7,018,364 B2 | 3/2006 | Giambattista |
| 7,104,972 B2 | 9/2006 | Moller |
| 7,169,132 B2 | 1/2007 | Bendek |
| 7,220,248 B2 | 5/2007 | Mernoe |
| 2001/0037087 A1 | 11/2001 | Knauer |
| 2005/0197625 A1 | 9/2005 | Haueter |
| 2007/0060894 A1 | 3/2007 | Dai |
| 2008/0114305 A1 | 5/2008 | Gerondale |

FOREIGN PATENT DOCUMENTS

| | | |
|---|---|---|
| JP | 2005-520646 A | 7/2005 |
| JP | 2005-537112 A | 12/2005 |
| JP | 2006-526467 A | 11/2006 |
| JP | 2012-511392 A | 5/2012 |

* cited by examiner

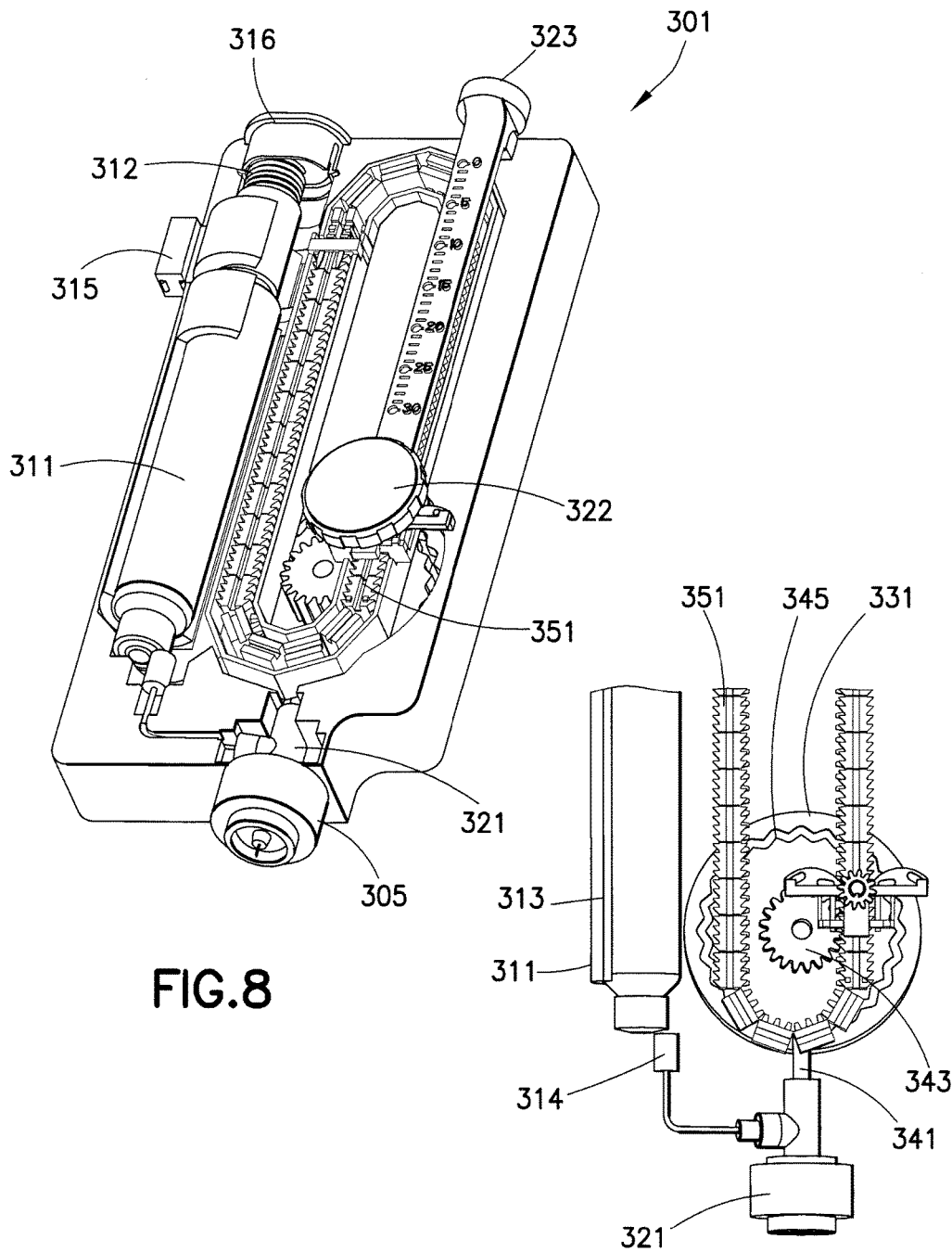

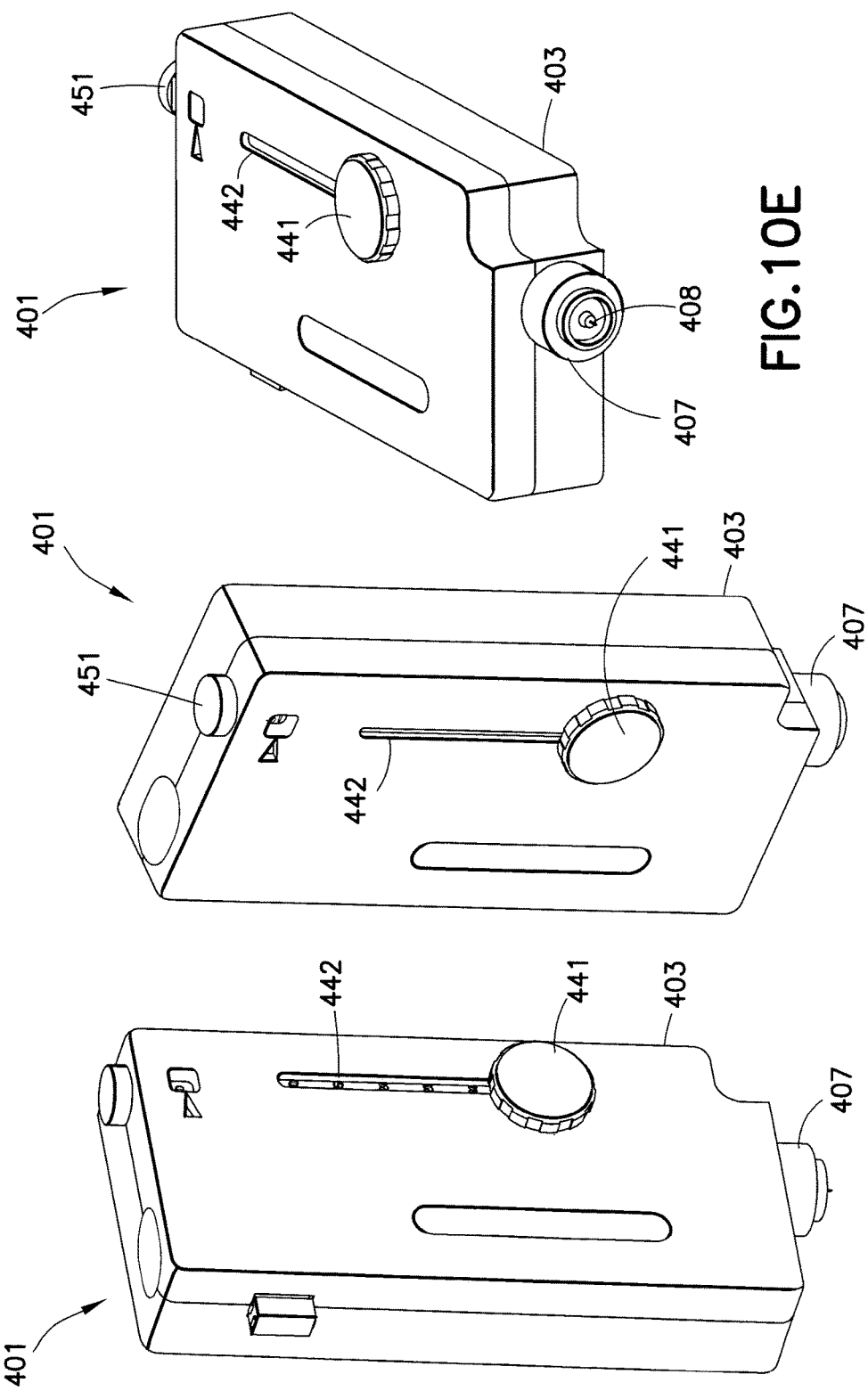

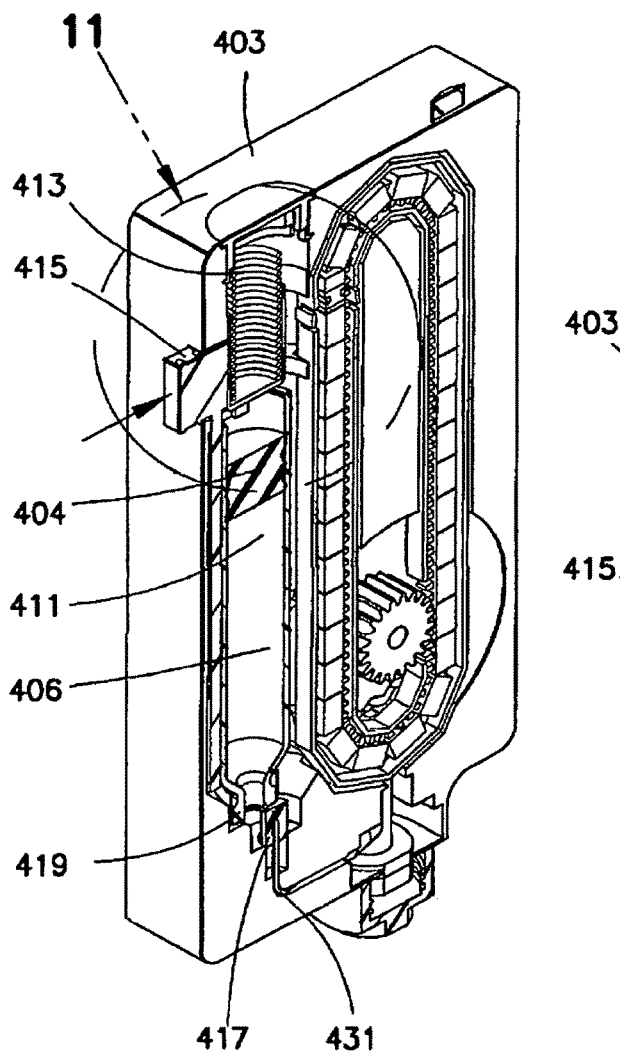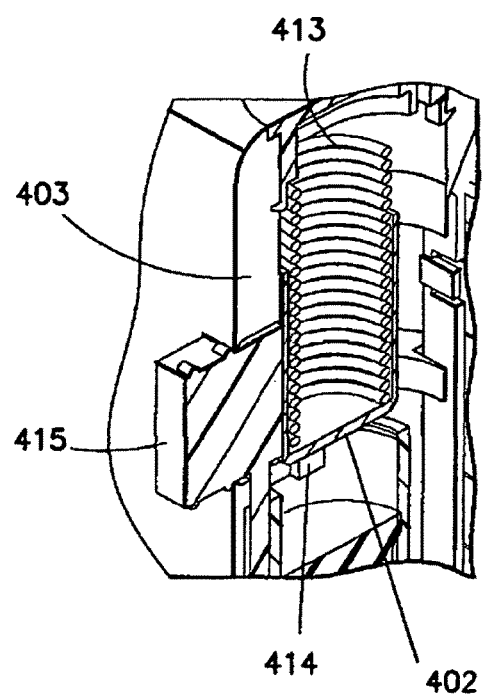
FIG. 11
FIG. 12

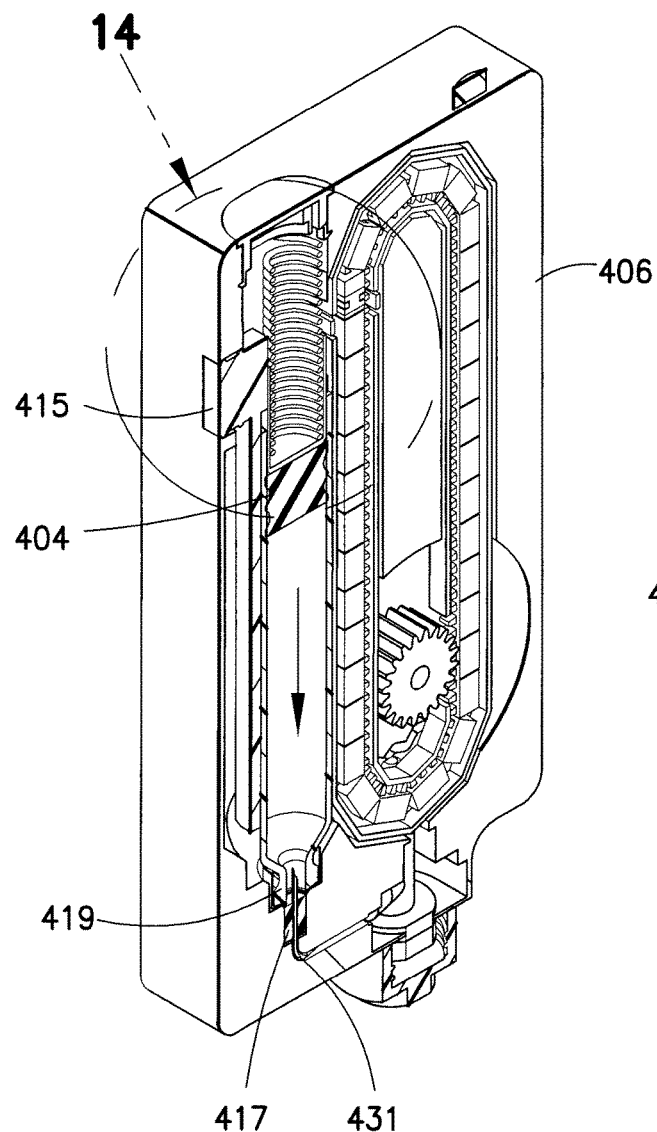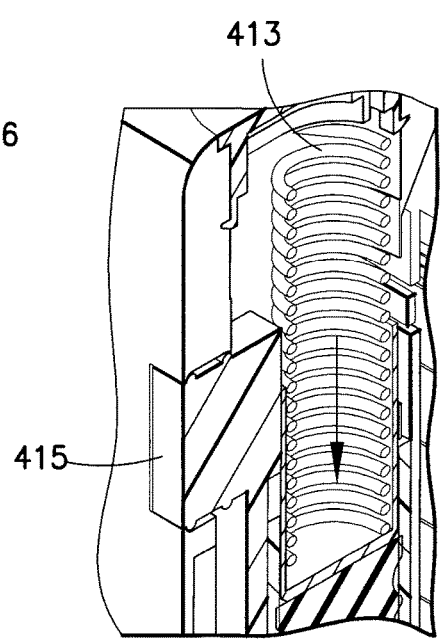
FIG.14
FIG.13

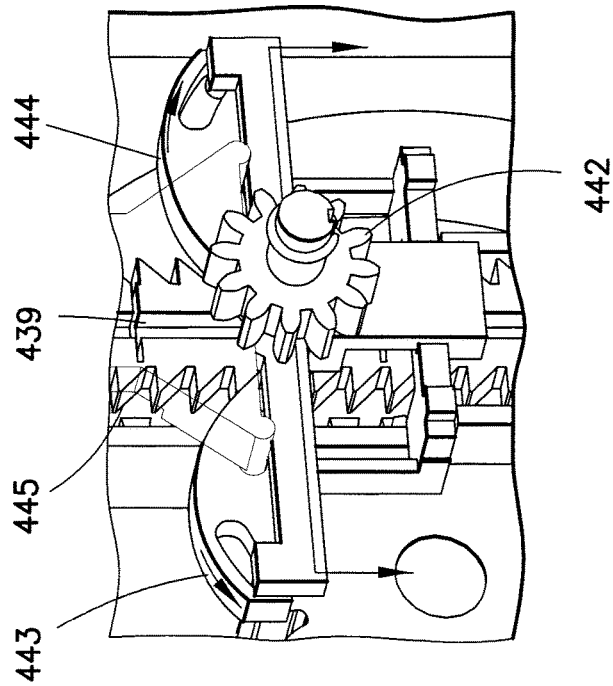
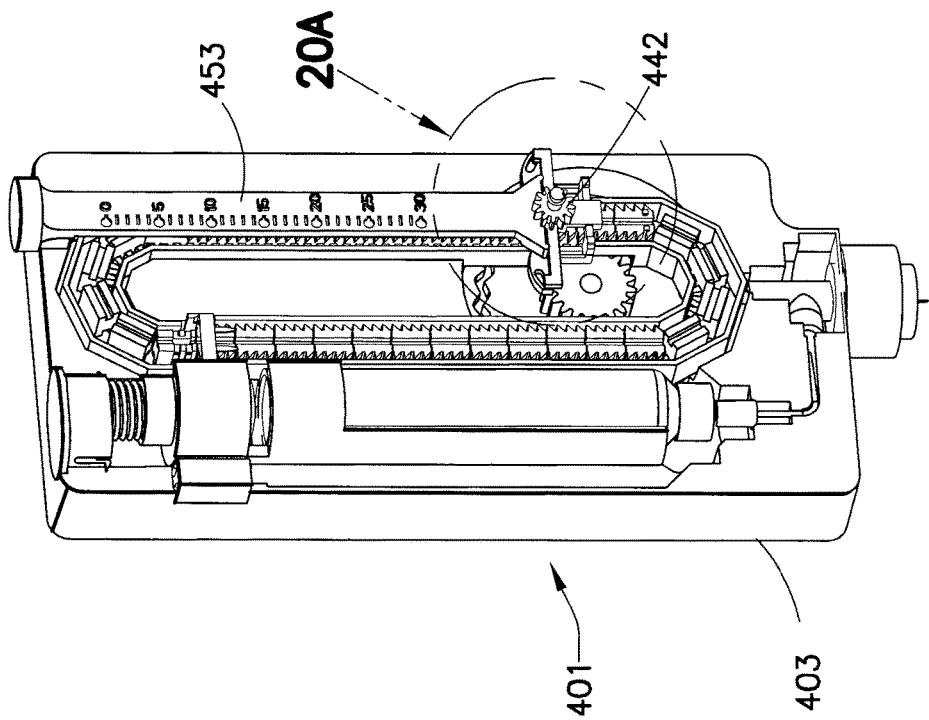

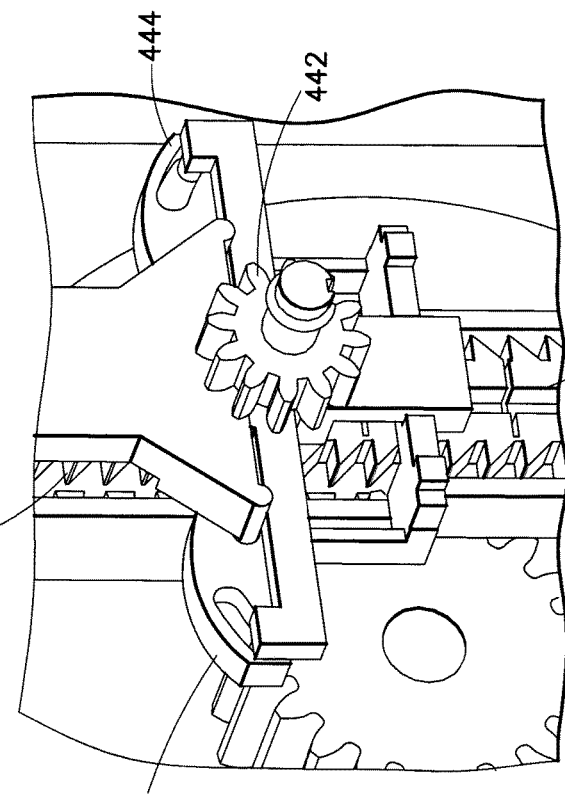
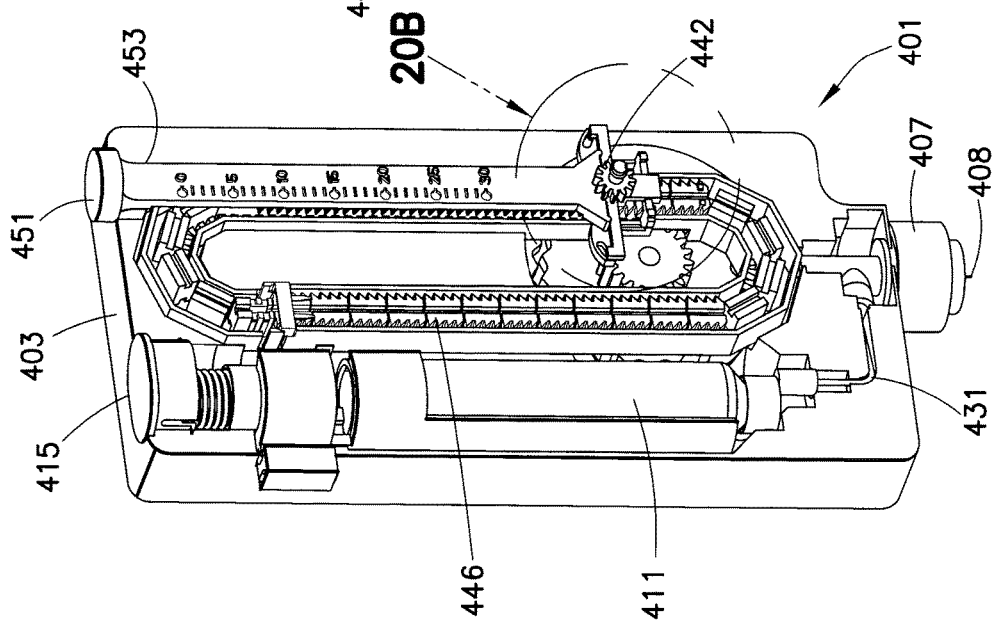
FIG. 20B
FIG. 19B

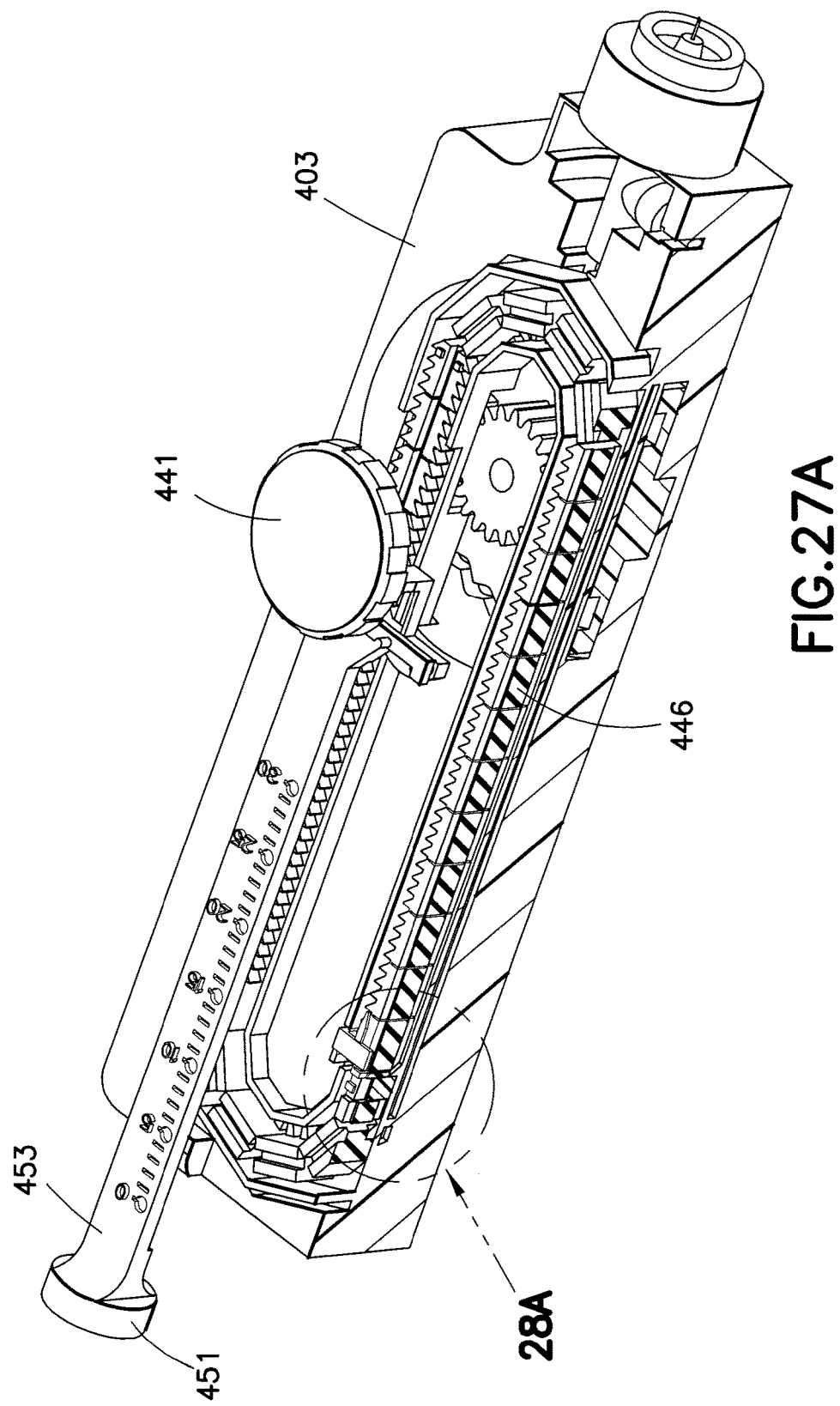

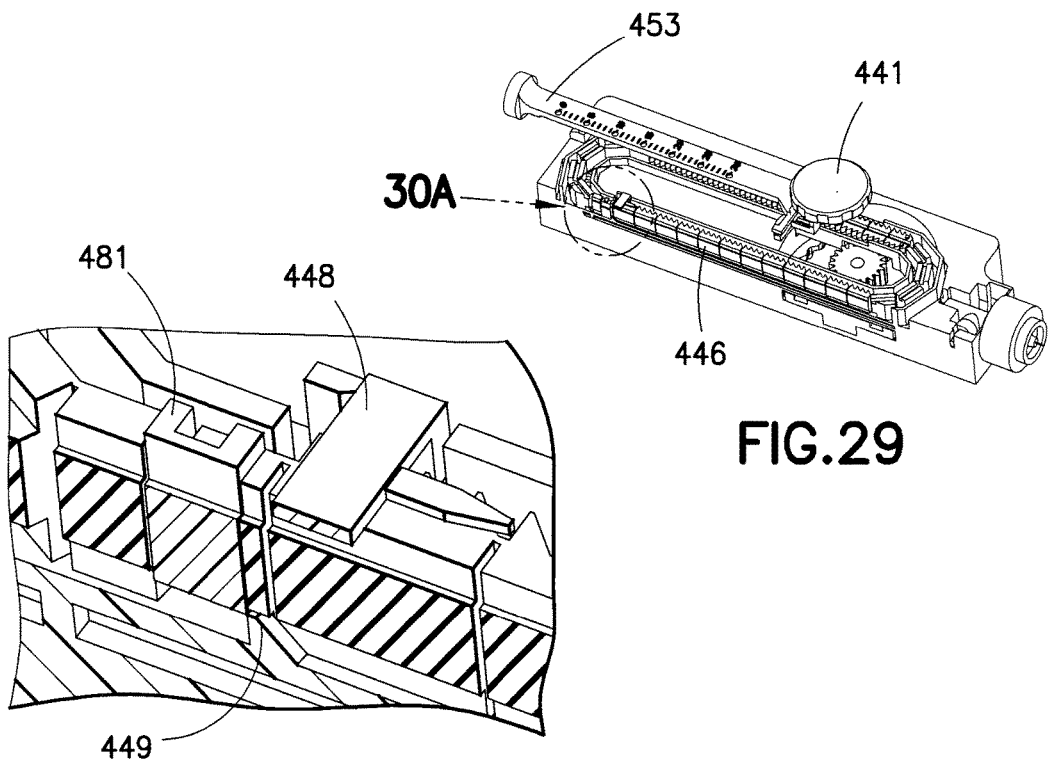
FIG. 29
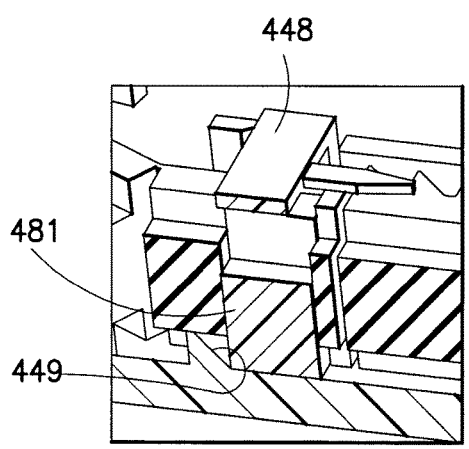
FIG. 30A
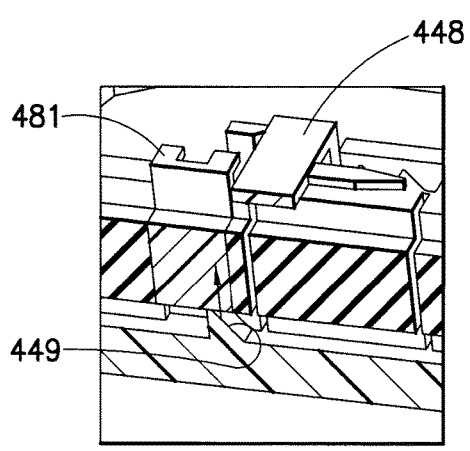
FIG. 30B
FIG. 30C

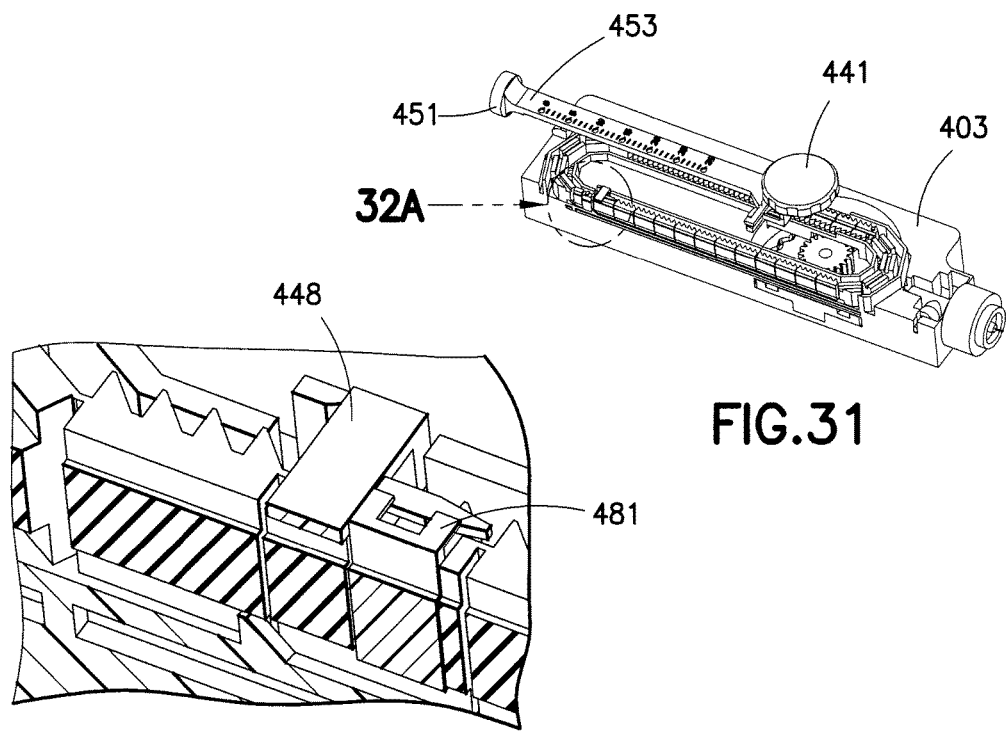
FIG.31
FIG.32A
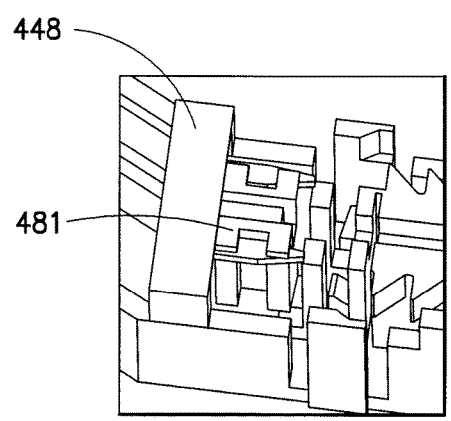
FIG.32B

MULTI-STROKE DELIVERY PUMPING MECHANISM FOR A DRUG DELIVERY DEVICE FOR HIGH PRESSURE INJECTIONS

CROSS REFERENCE TO RELATED APPLICATIONS

This application is a division of U.S. Nonprovisional application Ser. No. 12/998,840, filed Sep. 20, 2011, which is a U.S. national stage application under 35 U.S.C. § 371 of International Application No. PCT/US09/06421, filed Dec. 8, 2009, which claims the benefit under 35 U.S.C. § 119(e) of U.S. Provisional Application Ser. No. 61/193,594, filed Dec. 9, 2008, the entire disclosures of all of said prior applications being hereby incorporated by reference.

FIELD OF THE INVENTION

The present invention relates generally to a drug delivery device that facilitates high pressure medication injections. More particularly, the present invention relates to a drug delivery device that diverts high pressures away from the original drug container to prevent medicament leakage and inaccurate doses. Still more particularly, the present invention relates to injecting medication in small packets or pulses in succession to lower the force required to inject a medicament dose intradermally.

BACKGROUND OF THE INVENTION

Insulin and other injectable medications are commonly given with syringes into the intradermal layer of the skin and other dense tissues. Intradermal medication injections result in faster uptake of the medication, thereby resulting in improved therapy. Such injections require higher injection pressures, upwards of 200 psi, than traditional subcutaneous injections.

Techniques and devices are known for administering an injection into the intradermal region of the skin. One method, commonly referred to as the Mantoux technique, uses a "standard" needle and syringe, i.e., a syringe typically used to administer intramuscular or subcutaneous injections. The health care provider administering the injection follows a specific procedure that requires a somewhat precise orientation of the syringe with regard to the patient's skin as the injection is administered. The health care provider must also attempt to precisely control the penetration depth of the needle into the patient's skin to ensure that it does not penetrate beyond the intradermal region. Such a technique is complicated, difficult to administer, and often may only be administered by an experienced health care professional.

A conventional syringe 101 is shown in FIG. 1. The needle 103 is sufficiently long to deliver the drug to the subcutaneous region of the skin. However, a user would not be able to easily deliver the drug to the intradermal region of the skin, as discussed above.

Existing drug delivery pens offer several advantages over syringe-based systems for delivering insulin subcutaneously. Reusable drug delivery pens hold 20 or more doses without requiring the drug cartridge to be refilled. Dose setting is achieved simply with the use of a dial. However, those injection systems are designed for low pressure subcutaneous injections. Intradermal injection of insulin and other medications provides faster uptake of the drug, thereby leading to improved therapy. Existing drug delivery pens have several limitations regarding intradermal drug delivery.

First, the mechanical advantage provided by the pen is minimal and requires the user to supply upwards of 20 lbs of force to generate sufficient pressure. Second, the pen components can be damaged by this high force, resulting in leaking and inaccuracy at the high pressures.

Drug delivery pens, such as the exemplary drug delivery pen 100 shown in FIGS. 2 and 3, are designed for intradermal injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 3 is an exploded view of the drug delivery pen 100 of FIG. 2. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

The backpressure in subcutaneous injections is not very large, while the backpressure associated with intradermal injections may be many times greater than that of subcutaneous injections. Existing drug delivery pens require a large force to inject medication into the intradermal layer, thereby making the intradermal medication injection difficult. For example, the backpressure often exceeds 200 psi for an intradermal injection, while the backpressure for a subcutaneous injection is generally in the range of 30-50 psi. Thus, a need exists for a drug delivery pen that provides a mechanical advantage to facilitate an injecting a medicament dose intradermally. Furthermore, the drug delivery pen components can be damaged due to the high pressures associated with intradermal injections, thereby resulting in medication leakage and dose inaccuracy.

SUMMARY OF THE INVENTION

In accordance with an aspect of the present invention, a drug delivery device is provided that facilitates injecting insulin or other medicaments at high pressures.

In accordance with another aspect of the present invention, a drug delivery device has a secondary chamber that amplifies the injection force, thereby facilitating intradermal medication injections.

In accordance with yet another aspect of the present invention, high pressures associated with intradermal injections are diverted from the original medication container to prevent medication leakage and inaccurate doses.

In accordance with another aspect of the present invention, a drug delivery device is compact, thereby increasing usability and portability.

In accordance with another aspect of the present invention, a drug delivery device injects the medicament in small packets or pulses in succession to reduce the amount of pressure required to inject into an intradermal space.

In an exemplary embodiment of the present invention, the drug delivery device injects a medicament dose, such as insulin, at high pressures. The drug delivery device transports a user-determined bolus of the medicament from a primary container (or cartridge) to a secondary chamber using a fluid channel and a compression spring that provides a force on the cartridge stopper, thereby resulting in a positive pressure differential between the cartridge and the secondary chamber. This positive pressure ensures the filling of the secondary chamber, thereby allowing for the proper operation of the pumping system. A vacuum is not required in the secondary chamber during the pumping action, thereby preventing bubble creation in the medicament dose. The bolus is set by the user using a dial to select the desired medicament dose. The dial advances a lead screw that activates the pumping system once the injection is activated by a manual depression of the lead screw. The pumping system moves fluid in predefined packet volume of approximately 10 µl (1 unit of insulin) into the secondary chamber before injecting the fluid (medicament) into the patient. This is accomplished using a screw, nut, gear and cam set. The pumping action is repeated in packet size intervals until the set bolus is completely injected. The secondary chamber employs a smaller cross sectional area than the primary (original) medication container to amplify injection pressure at a given input force.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIG. 8 is a perspective view in cross section of the drug delivery device of FIG. 7;

FIG. 9 is a partial perspective view in cross section of the drug delivery device of FIG. 7 showing the flexible rack;

FIGS. 10A-10E are perspective view of a drug delivery device according to a third exemplary embodiment of the present invention;

FIGS. 11-14 illustrate priming and pressurization of the cartridge of the drug delivery device of FIG. 10;

FIGS. 15-20B illustrate the dose setting operation of the drug delivery device of FIG. 10;

FIGS. 26-34B illustrate the dose tracking operation of the drug delivery device of FIG. 10.

Throughout the drawings, like reference numbers will be understood to refer to like parts, components and structures.

DETAILED DESCRIPTION OF THE EXEMPLARY EMBODIMENTS

The drug delivery device according to exemplary embodiments of the present invention allows the user to inject a medicament dose at high pressures with lower input forces by decoupling the first chamber of a primary (original) medicament container and its cross sectional area from the injection mechanics.

Injecting a medicament dose in small packets or pulses, such as 10 µL, in succession, instead of at higher volumes can reduce the amount of pressure required for an intradermal injection. Reducing the pressure can result in less tissue damage and pain to the patient. Less pressure can also result in a lower required user force to intradermally inject the medication. Additionally, injecting a medicament dose in small doses or packets can provide improved dose accuracy over existing drug delivery pens, particularly at low dose ranges.

The presently disclosed drug delivery device has advantages in dose accuracy and medication leakage over existing drug delivery pens by diverting the high pressures associated with an intradermal injection away from the original drug container, particularly the stopper of the primary cartridge. At high pressures, the primary drug container stopper can deform, which can change the delivery volume and result in dose inaccuracies. Additionally, when the stopper is allowed to equilibrate and return to its natural volume after the needle is removed from the intradermal space and the back pressure dissipates, unwanted expulsion of the drug can occur.

Figure 4:
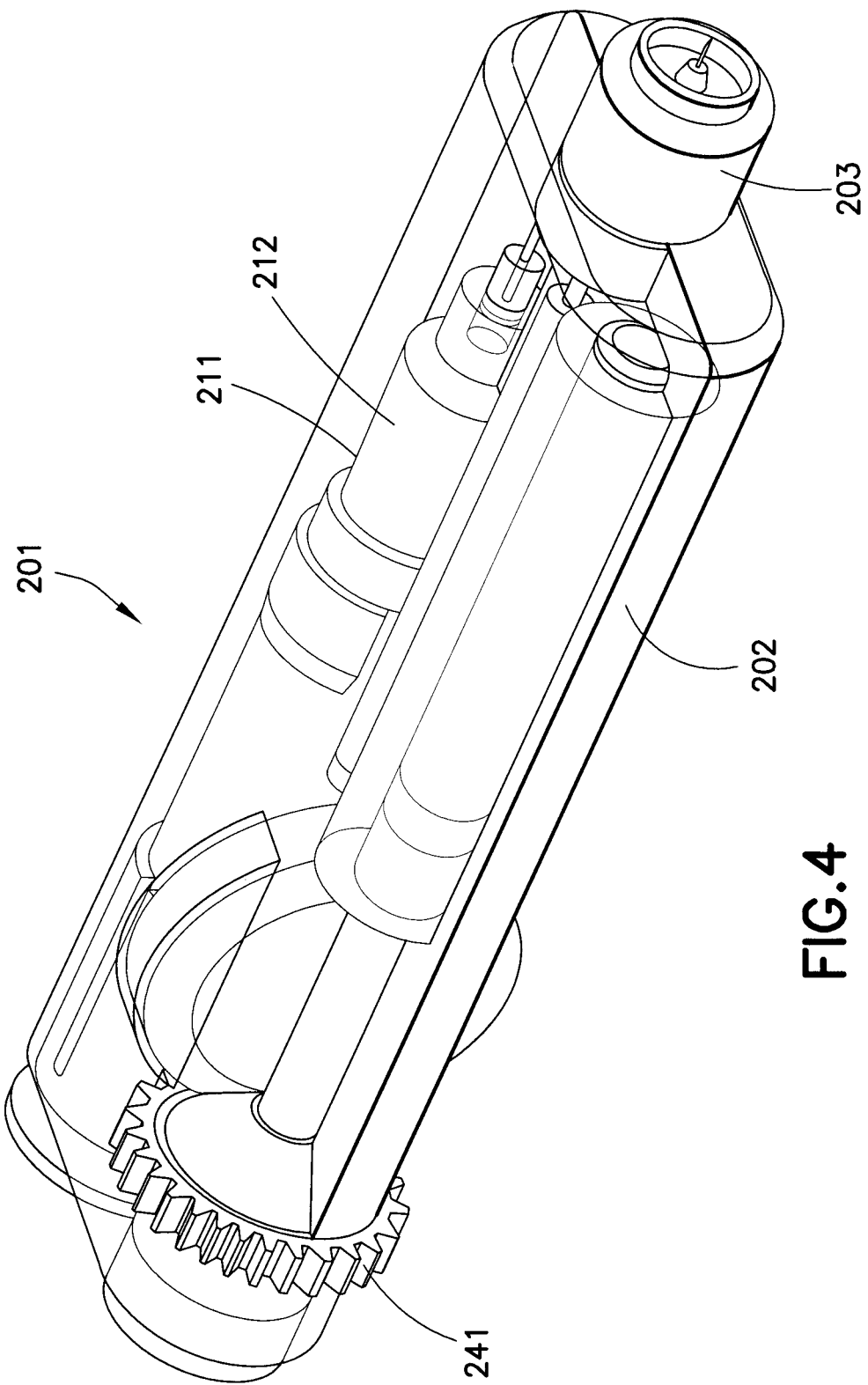
FIG. 4 is a perspective view of a drug delivery device according to a first exemplary embodiment of the present invention.
Figure 5:
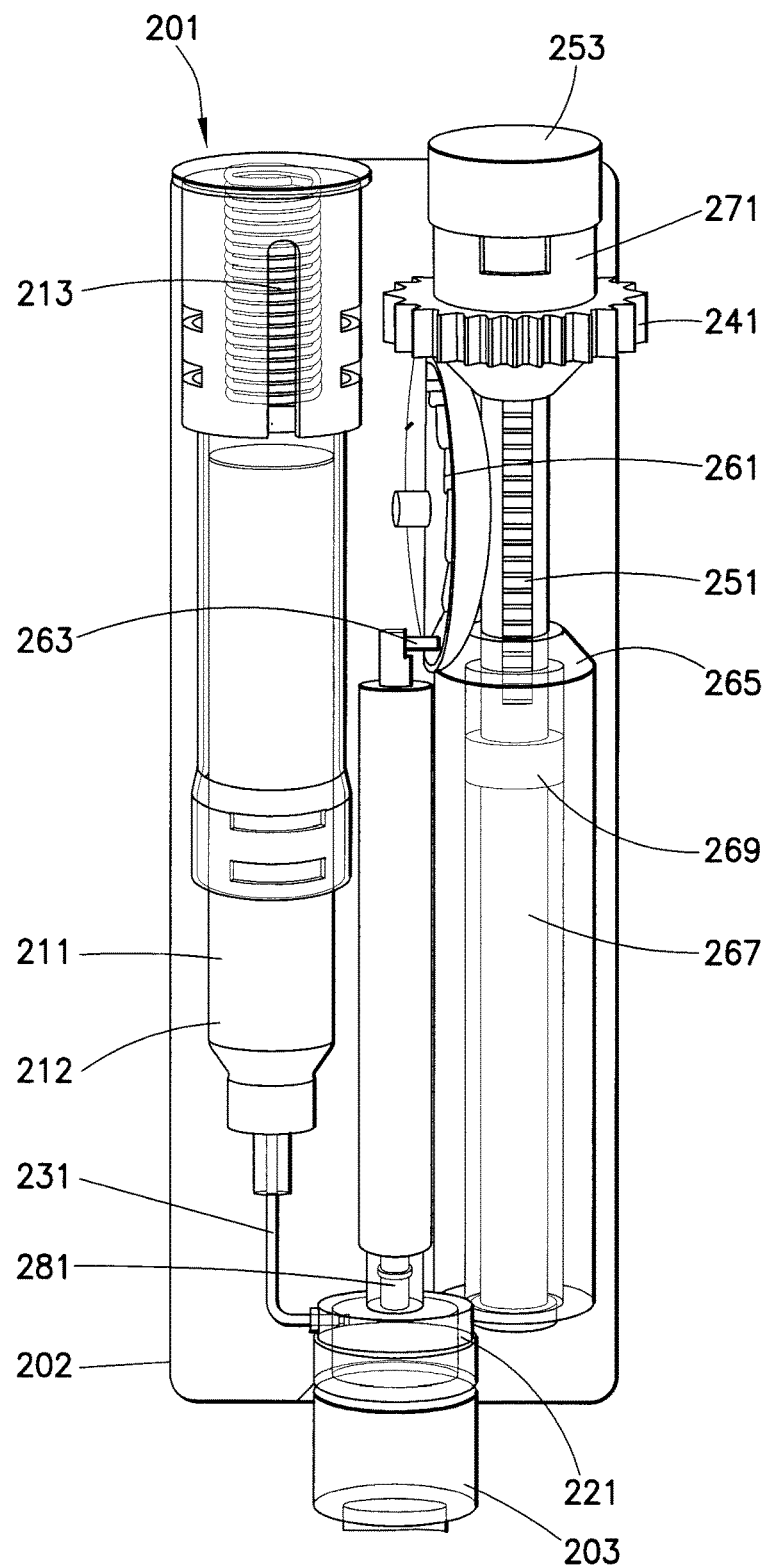
FIG. 5 is a perspective view in cross section of the drug delivery device of FIG. 4.
Figure 6:
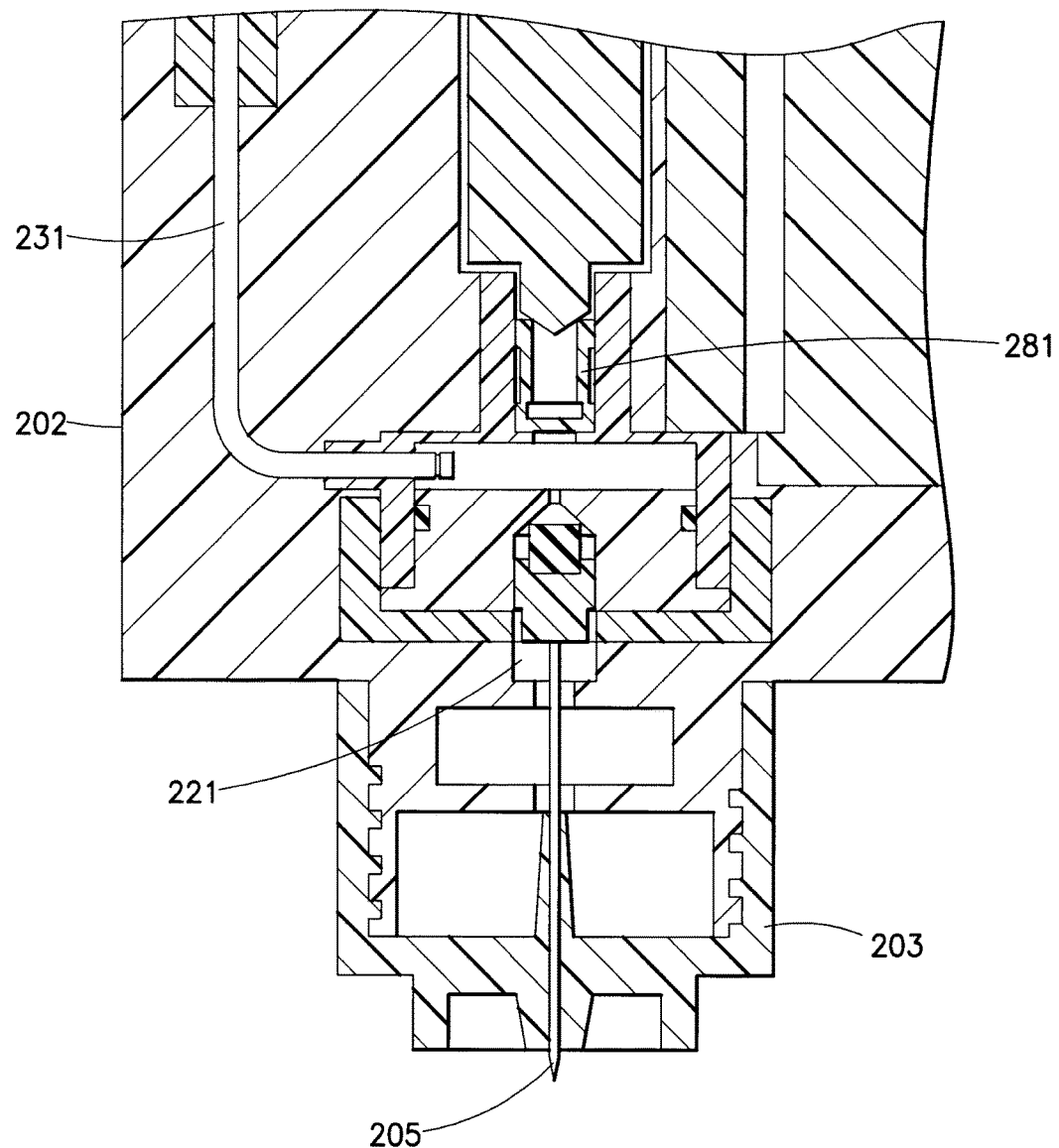
FIG. 6 is a partial front elevational view in cross section of the drug delivery device of FIG. 4.

In an exemplary embodiment of the present invention shown in FIGS. 4-6, a drug delivery device 201 injects a medicament, such as insulin, at high pressures. A needle hub 203 is threadably connected to a housing 202. A needle 203 is rigidly fixed in the needle hub 203 and is in communication with the second chamber 221. Preferably, the needle 202 is an intradermal needle. Alternatively, the needle may be a subcutaneous needle. Preferably, the needle is a small gauge needle, such as a 34 gauge needle. The drug delivery device according to exemplary embodiments of the present invention injects insulin, high viscosity medicaments, or other medicaments at high pressures.

The drug delivery device 201 transports a user-determined bolus of the medicament from a first chamber 211 of a primary container (or cartridge 212) to the second chamber 221 using a fluid channel 231 and a compression spring 213 that provides a force on the cartridge stopper 214, thereby resulting in a positive pressure differential between the first chamber 211 and the second chamber 221. This positive pressure ensures the filling of the second chamber 221, thereby allowing for the proper operation of the pumping system. A vacuum is not required and is preferably not created in the second chamber 221 during the pumping action, thereby preventing bubble creation in the medicament dose. The bolus is set by the user using a dial 241 to select a desired dose. The dial 241 advances a lead screw that activates the pumping system once the injection is activated by a manual depression of the lead screw. The pumping system moves fluid in a predefined packet volume of approximately 10 µl (1 unit of insulin) into the second chamber 211 before then injecting the fluid (medicament dose) into the patient. This is accomplished using a screw, nut, gear and cam set. The pumping action is repeated in packet size intervals until the set bolus is completely injected. The second chamber 221 employs a smaller cross sectional area than the first chamber 211 of the cartridge to amplify injection pressure at a given input force.

As shown in FIGS. 4-6, the injection pressure is decoupled from the first chamber 211 of the cartridge 212 by moving the fluid to a second chamber 221 via a pumping cam system. The second chamber 221 has a smaller cross sectional area than the first chamber 211 of the cartridge 212, thereby providing a higher pressure for the same user input force. Using the relationship of pressure, force and area, P=F/A, a chamber with half the cross sectional area produces twice the injection pressure at a given input force.

Figure 21:
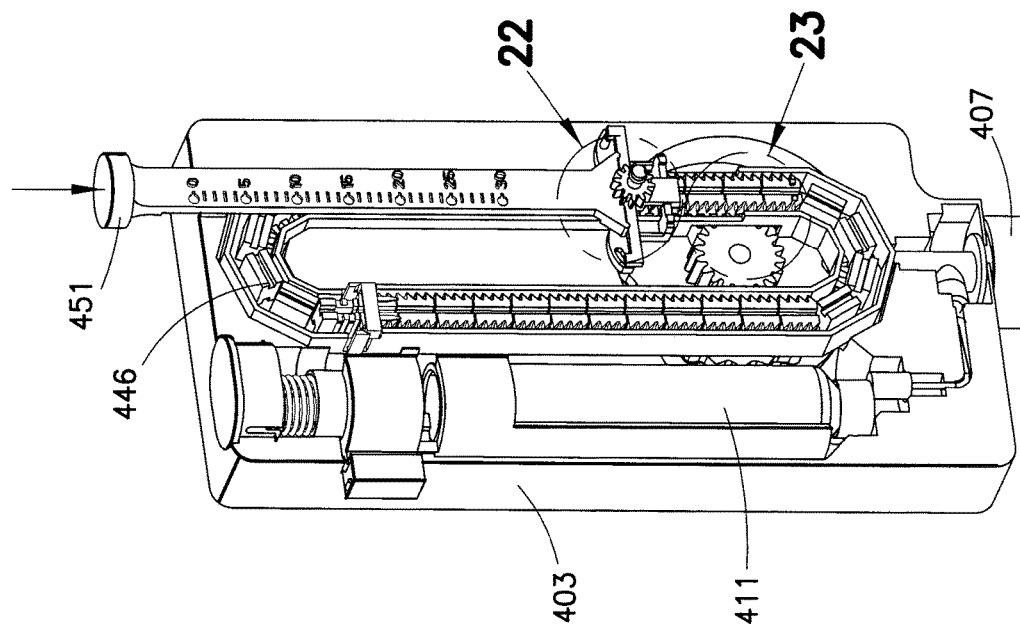

The medicament dose is set by rotating a dose setting member, a dose setting wheel 241 as shown in FIG. 4, which is connected to the drive screw 251. Rotation of the dose setting wheel 241 to set the medicament dose causes the drive screw 251 to move upwardly out of the housing 202 from a first position (FIG. 5) to a second position (FIG. 21). A dose tracker nut 265 is disposed on the drive screw 251 and remains stationary on the drive screw as it is being moved upwardly out of the housing 202 as the medicament dose is being set. When the medicament dose is being delivered, the drive screw 251 slides through the dose tracking nut 263 such that the dose tracking nut moves upwardly on the drive screw. When the dose tracking nut 263 abuts the upper end 265 of the dose tracking housing 267, the drive screw 251 is prevented from being moved upwardly out of the housing 202 by the upper end 265 of the dose tracking housing 267, thereby preventing a further medicament dose from being set.

A bevel gear 261 is rotatably engaged with the dose setting wheel 241. A clutch 271 separates the dose setting wheel 241 from the bevel gear 261 when the dose is being set. The bevel gear 261 has a cam shaft 263 connected to a piston 281. Rotation of the bevel gear 261 causes the piston 281 to move up and down in a reciprocating motion with rotation of the cam shaft 263. Upward movement of the piston 281 draws a small portion or packet of the medicament dose from the first chamber 211 into the second chamber 221. The downward movement of the piston 281 expels the packet of the medicament dose in the second chamber 221 out through the needle 205.

When the medicament dose has been set, the button 253 at an end of the drive screw 251 is pushed downwardly by the user to inject the medicament dose. As the drive screw 251 is moved downwardly through the housing, the clutch 271 causes the dose setting wheel 241 to engage the bevel gear 261, thereby rotating the bevel gear. As the bevel gear 261 rotates, the cam shaft 263 drives the piston 281 up and down in a reciprocating manner, thereby injecting the medicament dose through several smaller sequential packet medicament dose injections. The travel distance of the drive screw 251 corresponds to a predetermined number of sequential packets to be injected. The total number of sequential medicament dose packets injected corresponds to the set medicament dose, which is accomplished by a single movement of the drive screw 251 from the second position to the first position.

Preliminary animal studies have demonstrated that the size of an injection bolus has an effect on the resulting injection back pressure when injecting into the intradermal space. Smaller doses produced reduced back pressure during intradermal injections than larger boluses. Injecting medicament using 1 unit (10 µL) pulses, the peak back pressure for an intradermal injection (and hence the peak injection pressure that must be applied) may be reduced by reducing the amount of dermis that must yield during injection at any particular instant.

Improved dose accuracy and reduced "drooling" issues related to cartridge stopper effects under high pressure also result from decoupling the high injection pressure associated with an intradermal injection from the first chamber 211 of the cartridge 212.

Figure 1:
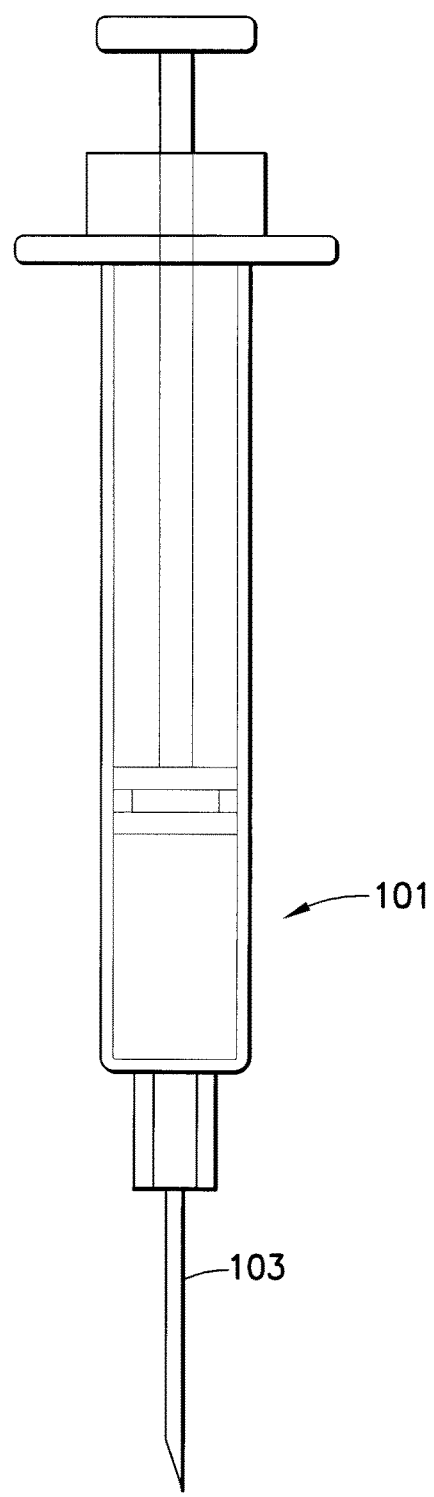
FIG. 1 is a front elevational view of a syringe.
Figure 2:
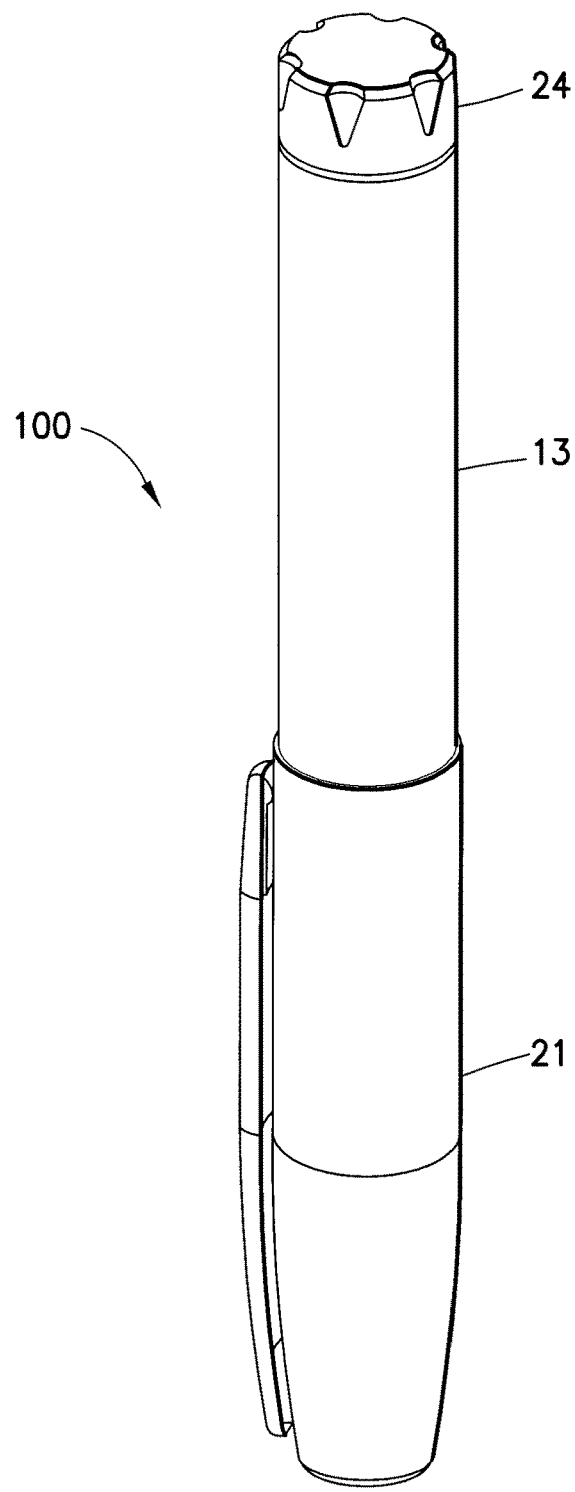
FIG. 2 is a perspective view of a drug delivery pen.
Figure 3:
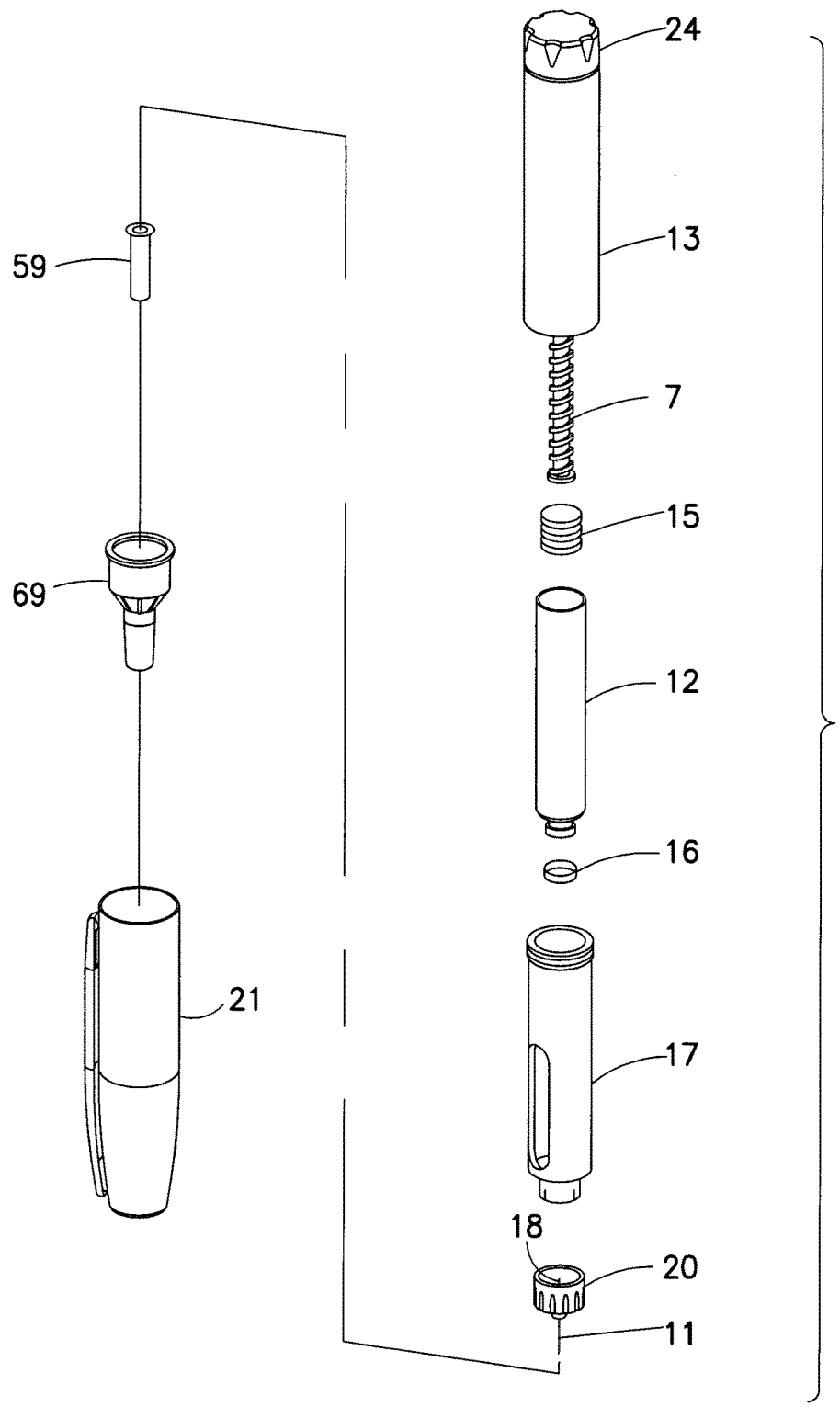
FIG. 3 is an exploded perspective view of the drug delivery pen of FIG. 2.

A lower pressure is maintained in the cartridge 211 by moving the injection fluid into the second chamber 221 prior to an injection. This allows a high pressure injection to occur without causing high pressures in the first chamber 211 of the cartridge 212. In most existing drug delivery pens, the delivered medicament dose results from a linear displacement of a drive screw 7 (FIG. 3) that translates a given length dependent on the dialed bolus volume. The dialed bolus determines the stroke length of the injection. The user imparts a force on the injection button and completes the stroke length of the injection. The force and stroke of the injection motion are translated into a torque. The torque is then used to drive the drive screw 7 (FIG. 3) linearly forward. That type of system can produce medicament dose inaccuracies at the low end of the dosing range as the relationship between the initial stroke and the final drive screw motion.

Figure 7:
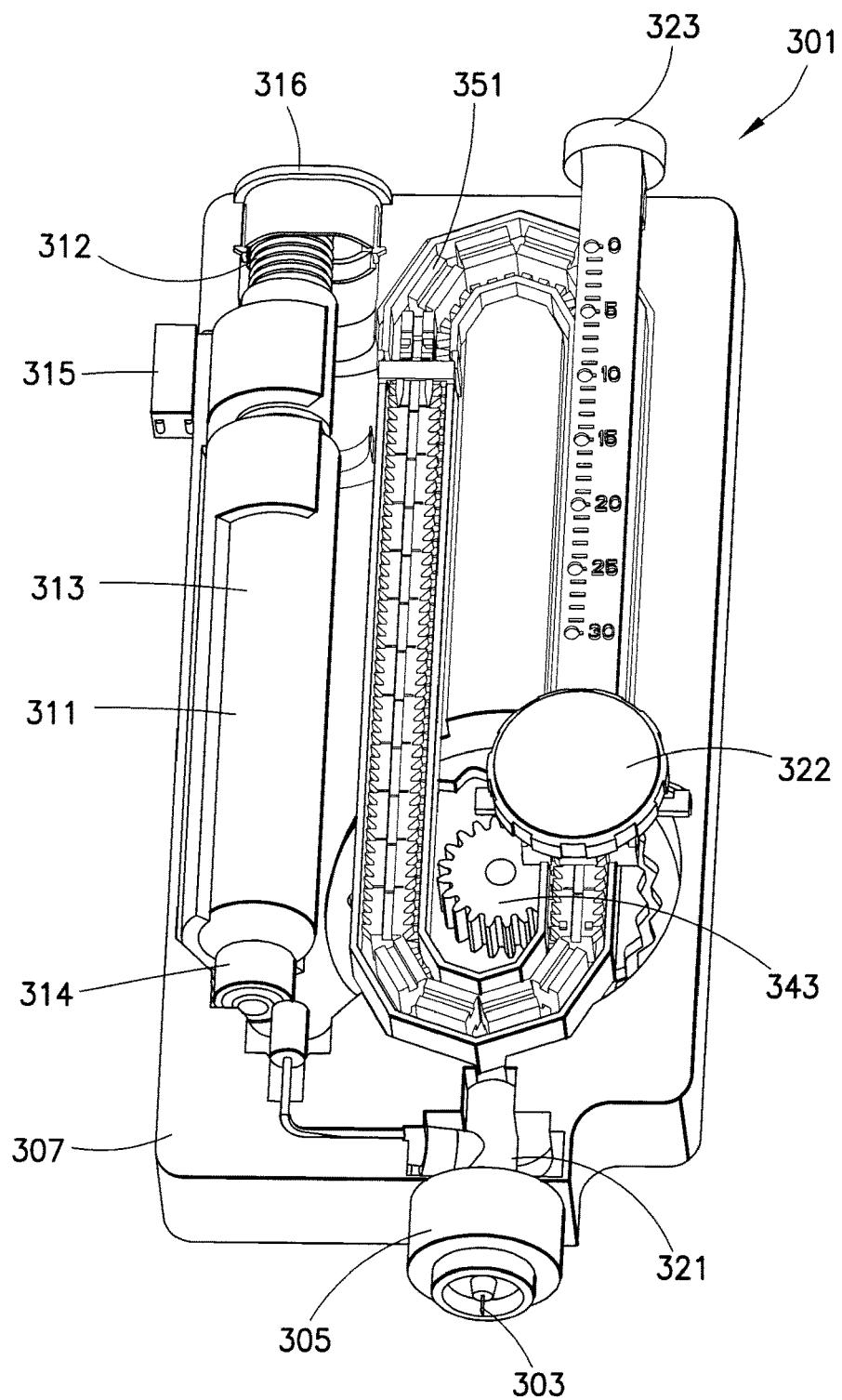
FIG. 7 is a perspective view in cross section of a drug delivery device according to a second exemplary embodiment of the present invention.

Alternatively, as shown in FIGS. 7-9, a drug delivery device 301 according to a second exemplary embodiment of the present invention employs a full-rack 351 to drive a cam wheel 331. The full-rack 451 is a continuous, non-ending rack. The basic functionality and underlying technical principles of the drug delivery device 301 of the second exemplary embodiment are substantially similar to the drug delivery device 201 of the first exemplary embodiment.

A cartridge 311 has a first chamber for storing a medicament. When the cartridge 311 is first inserted in the housing 307, the cartridge 311 is disposed in a first position as shown in FIG. 7. A needle hub 305 is connected to the housing 307 such that a needle 303 rigidly fixed to the needle hub 305 is in communication with the second chamber 321.

In the first position, the cartridge 311 is separated from a septum-piercing needle 314. A priming button 315 extends outwardly from the housing 307 when the cartridge 311 is in the first position. A user pushes the priming button 315 inwardly, thereby moving a spring housing 316 sideways away from an obstruction, such that the compression spring 312 is released. The compression spring 312 expands and engages a stopper disposed in the cartridge 311. The force of the compression spring 312 on the cartridge 311 moves the cartridge into the second position, as shown in FIG. 8, in which the septum-piercing needle 314 pierces the septum of the cartridge 311. The movement of the cartridge 311 to the second position pressurizes the cartridge 311.

A dose setting wheel 322 is rotated to set a medicament dose. Rotation of the dose setting wheel 322 moves an injection rod 323 upwardly a distance that corresponds to the medicament dose being set. During injection, the rod 323 is depressed by the use, thereby engaging the clutch and turning the cam wheel 331. The rotation of the cam wheel 331 drives the piston 341 in a reciprocating (pumping) motion, pushing the fluid out on the downstroke, and allowing the second chamber 321 to fill from the first chamber 313 of the pressurized cartridge 311 on the upstroke.

The cam wheel 341 has a cam gear 343 for engaging the rack 351. Downward movement of the injection rod 323 moves the rack 351 clockwise as shown in FIGS. 7-9. The clockwise rotation of the rack 351 causes the cam gear 343 to rotate clockwise, which rotates the cam wheel 341 clockwise. A cam curve 345 disposed on the cam wheel 341 engages the piston, thereby reciprocatingly moving the piston 341.

Figure 9B:
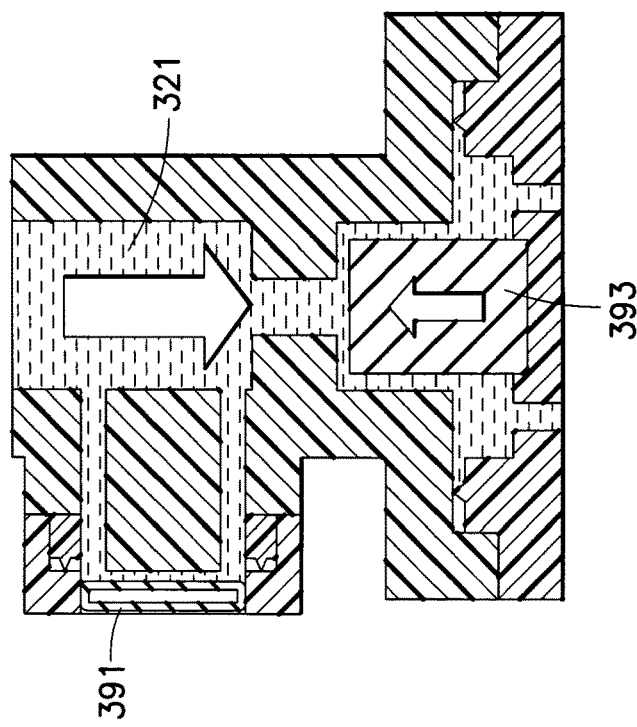
FIGS. 9A and 9B are schematics of a valve system for a second chamber of the drug delivery device.
Figure 9A:
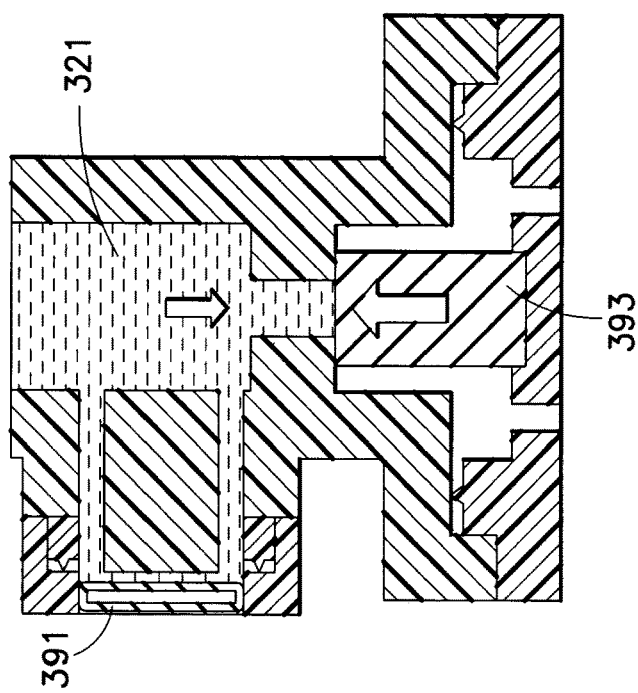

The force of the piston down stoke closes a first valve, $V_1$, 391 (located at the fluid inlet to the second chamber 321) during the injection because the force to deflect the valve shoulder is less than the stopper friction, and then opens the first valve, $V_1$, 391 during the upstroke for filling of the second chamber 321. Any suitable valve may be used. A schematic of the valve system is shown in FIGS. 9A and 9B.

A second valve, $V_2$, 393 (located at the fluid exit of the second chamber 321) opens only during injection when the pressure in the second chamber 321 is high enough to compress the second valve 393, thereby opening the seal and allowing fluid to travel to the needle 303.

The drug delivery devices according to the first and second exemplary embodiments shown in FIGS. 4-9 have an integrated dose tracking system that prevents dose setting when the medicament volume is limited. As shown in FIGS. 7-9, a full rack embodiment features a reusable rack 351 that is mechanically triggered during its third cycle to effectively track the dose and prevent dose setting as the first chamber 313 of the cartridge 311 is emptied.

The second chamber 321 has a smaller cross sectional area than the cartridge 31, thereby providing a higher pressure using the same user input force. A standard 3.0 mL insulin cartridge has a diameter of approximately 9.7 mm, thereby resulting in a cross sectional area of $A=\pi r^2=4.85^2*3.14159=73.9$ mm$^2$. In a preferred embodiment, the second chamber 321 of the drug delivery device 301 has a diameter of 3.5 mm resulting in a cross sectional area of $1.75^2*3.14159=9.62$ mm$^2$. For a given pressure, P, a force multiplication is achieved using the following relationships: $P=F_1/A_1$, $P=F_2/A_2$. Therefore, $F_1/A_1=F_2/A_2$. The force multiplier $M_f$, $F_1/F_2$ becomes the ratio of the areas, $A_1/A_2$, $M_f=73.9/9.62=7.7$, with an efficiency, $\eta$, of 100%.

Therefore, without taking friction in the system into account ($\eta=100\%$), this preferred embodiment of the drug delivery device would require approximately seven (7) times less force to achieve the same injection pressure as a device that applies force directly to the primary insulin container (cartridge).

Taking friction into account, however, the force multiplier is slightly reduced. The drug delivery device according to the first exemplary embodiment (FIGS. 4-6 with a nut/screw drive), features an efficiency of about 50-60%, which results in an injection pressure of about 100-120 psi ($M_f=3-3.5$) for the preferred embodiment. The drug delivery device according to the second exemplary embodiment (FIGS. 7-9 with a full rack), has a higher efficiency than the first exemplary embodiment and produces an injection pressure of about 150-180 Psi ($M_f=5-6$) for the preferred embodiment. This efficiency increase is due to the lower friction of the rack (FIGS. 7-9) when compared to the nut/screw drive (FIGS. 4-6).

A third exemplary embodiment of a dual-chambered drug delivery device 401 of the present invention is shown in FIGS. 10-36. The drug delivery device 401 operates substantially similarly to the drug delivery device 301 according to the second exemplary embodiment shown in FIGS. 7-9. The drug delivery device 401 allows priming and pressurization of the cartridge, setting the medicament dose, delivering the medicament dose, and tracking the dose. A needle hub 407 is connected to the device housing 403. A needle 408 is rigidly fixed to the needle hub 408 and communicates with a second chamber 421 to deliver a medicament dose.

FIGS. 11-14 illustrate the operation of cartridge priming and pressurization. When the drug delivery device 401 is shipped, a compression spring housing 402 sits on a ledge 414 of the device housing 403, as shown in FIGS. 11 and 12. An end of a compression spring 413 engages the compression spring housing 402. The other end of the compression spring 413 engages an inner surface of the device housing 403, such that the compression spring 413 is in a compressed position. Pushing a priming button 415 inwardly moves the spring housing 402 off the ledge 414, as shown in FIGS. 13 and 14. The compression spring 413 expands until the compression spring housing 402 engages the stopper 404 within the cartridge 411. The force of the compression spring 413 on the cartridge stopper 404 causes the cartridge 411 to move from a first position shown in FIGS. 11 and 12 in which the cartridge septum 419 is separated from the septum-piercing needle 417 to a second position shown in FIGS. 13 and 14 in which the septum-piercing needle 417 pierces the cartridge septum 419.

When the compression spring 413 is engaging the cartridge stopper 404 and the septum-piercing needle 417 is piercing the cartridge septum 419, the cartridge 411 is primed and pressurized. Medicament stored in a first chamber 406 of the cartridge 411 is now able to enter the fluid conduit 431. When a depleted cartridge 411 is removed from the housing 403, insertion of the replacement cartridge 411 returns the priming button 415 to a position extending outwardly of the housing as shown in FIGS. 11 and 12.

Figure 16:
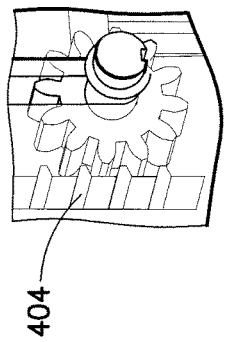
Figure 15:
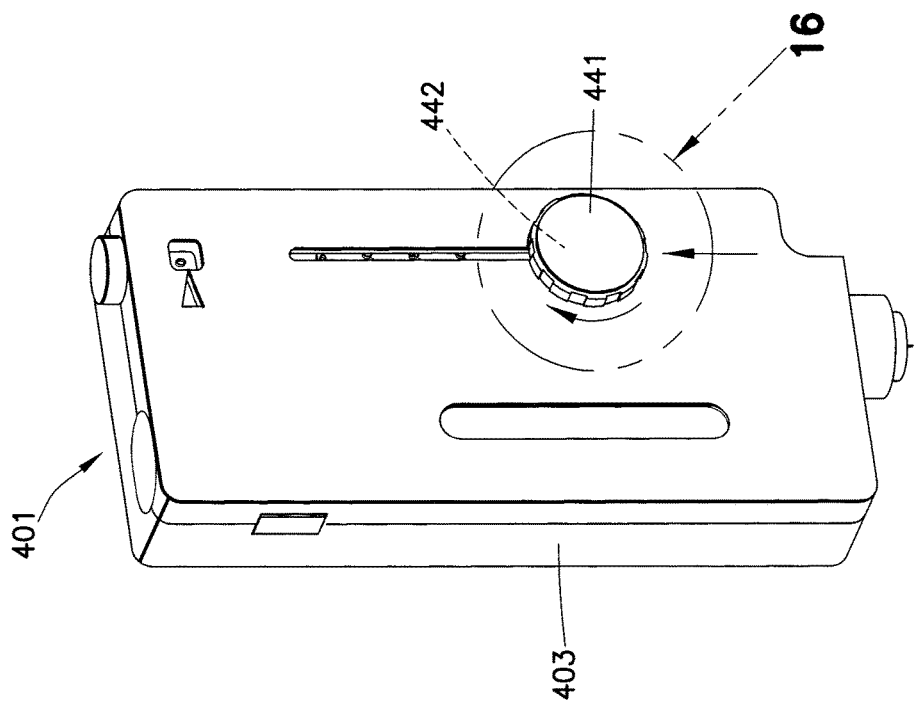
Figure 18:
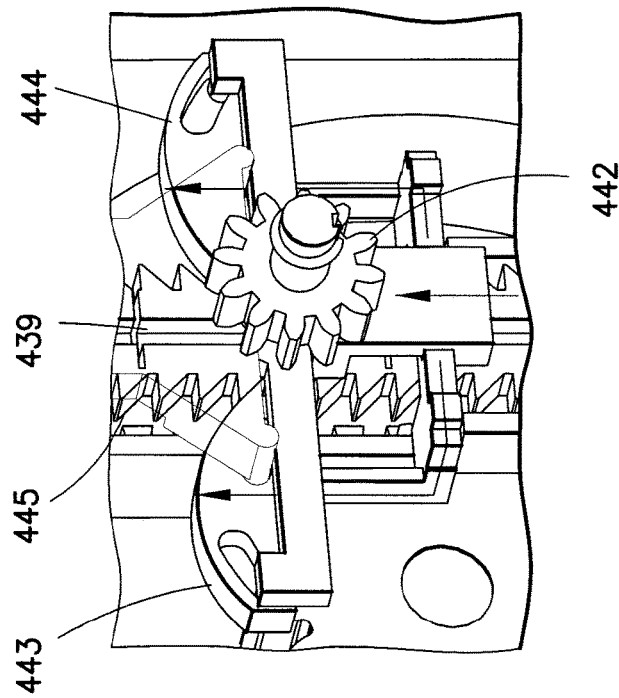
Figure 17:
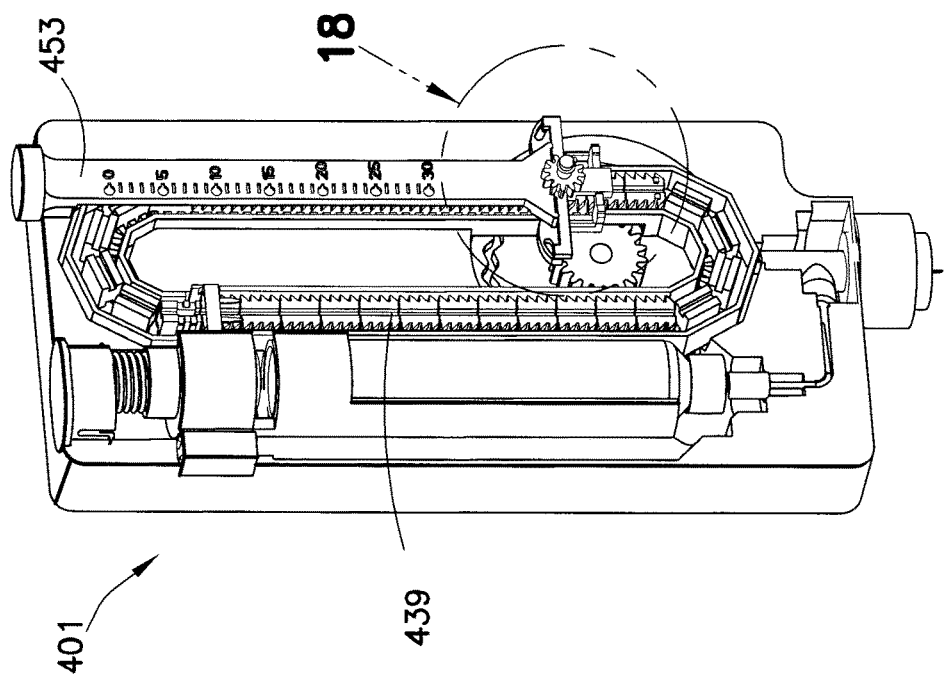
Figure 22:
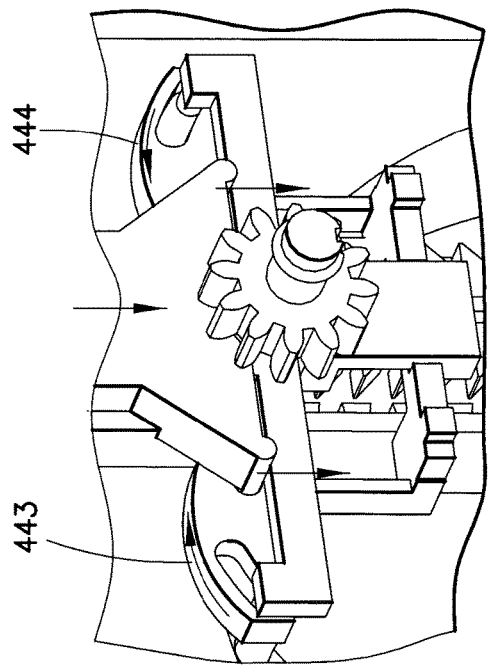
FIGS. 21-25 illustrate delivering the dose with the drug delivery device of FIG. 10.
Figure 23:
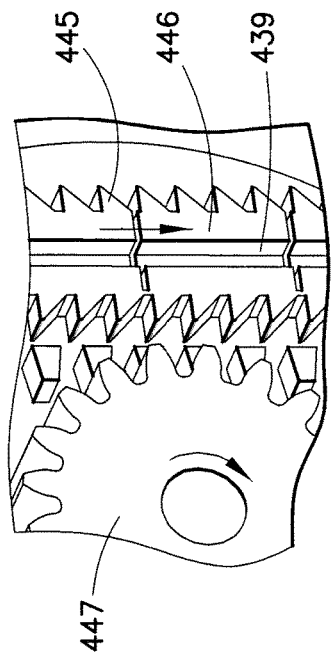

FIGS. 15-20 illustrate setting a medicament dose with the drug delivery device 401. A dose setting wheel 441 has a gear 442 that engages teeth 404 of the housing 403, as shown in FIGS. 15 and 16. Increasing the dose setting with the dose setting wheel (rotating the dose setting wheel clockwise as shown in FIG. 15) clicks the ratchet teeth 443 and 444 over the rack teeth 445, as shown in FIGS. 17 and 18, thereby moving the dose setting wheel 441 upwardly in the housing groove 440 and the rack groove 439. Upward movement of the dose setting wheel 441 moves the ratchet 453 upwardly from a first position shown in FIG. 15 to a second position shown in FIG. 21, such that a button 451 on an end of the ratchet is accessible to the user outside of the housing 403.

To correct a medicament dose, the dose setting wheel 441 is rotated counter-clockwise as shown in FIG. 15. Dose correcting flexes the ratchet teeth 443 and 444 outwardly such that the ratchet teeth 443 and 444 disengage the rack teeth 445, thereby allowing the dose setting wheel 441 and ratchet 453 to move downwardly without moving the rack 446, as shown in FIGS. 19 and 20. The ratchet 453 is fixed to the dose setting wheel 441 such that the ratchet 453 and dose setting wheel 441 move together.

Figure 10A:
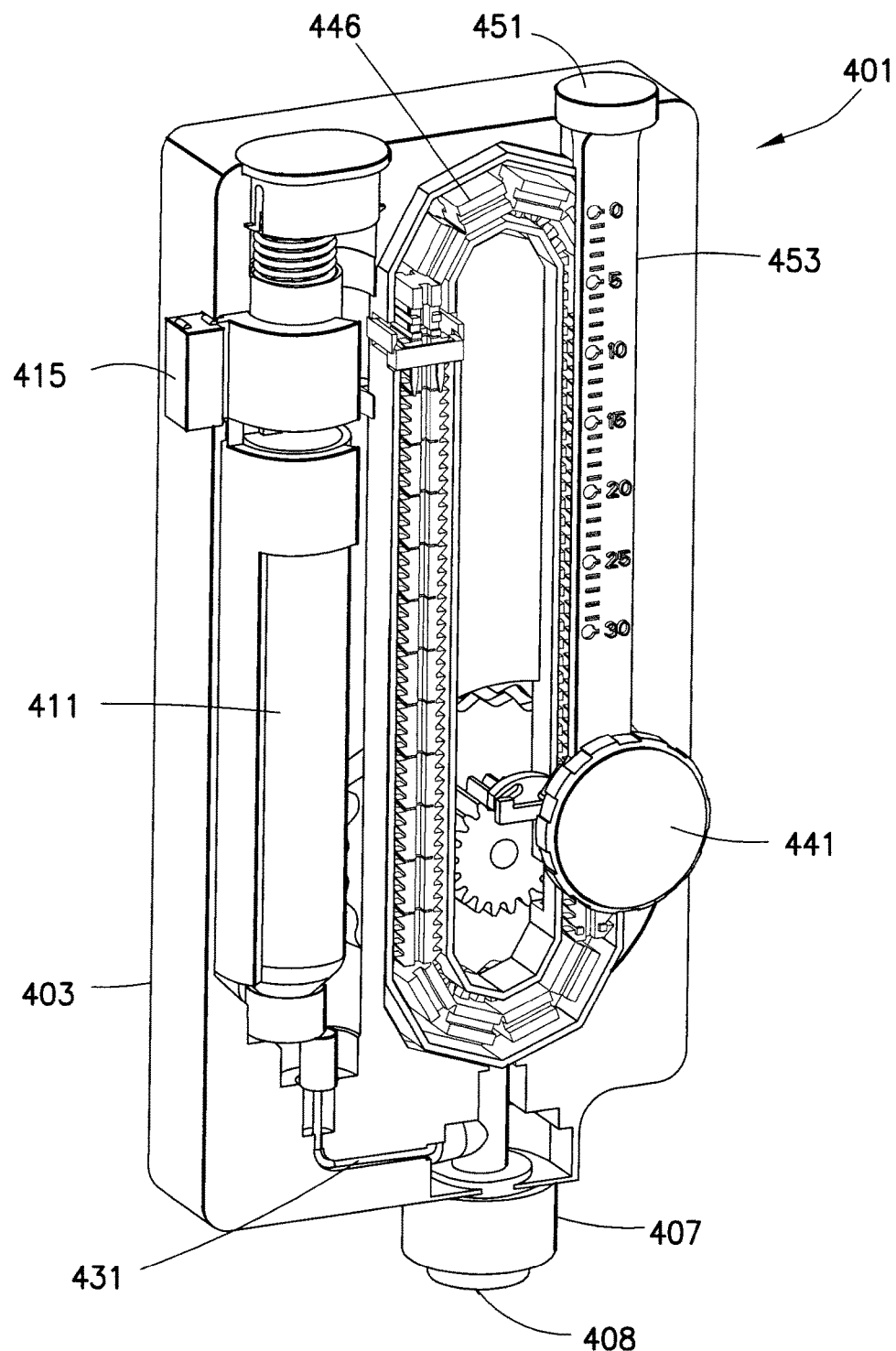
Figure 10B:
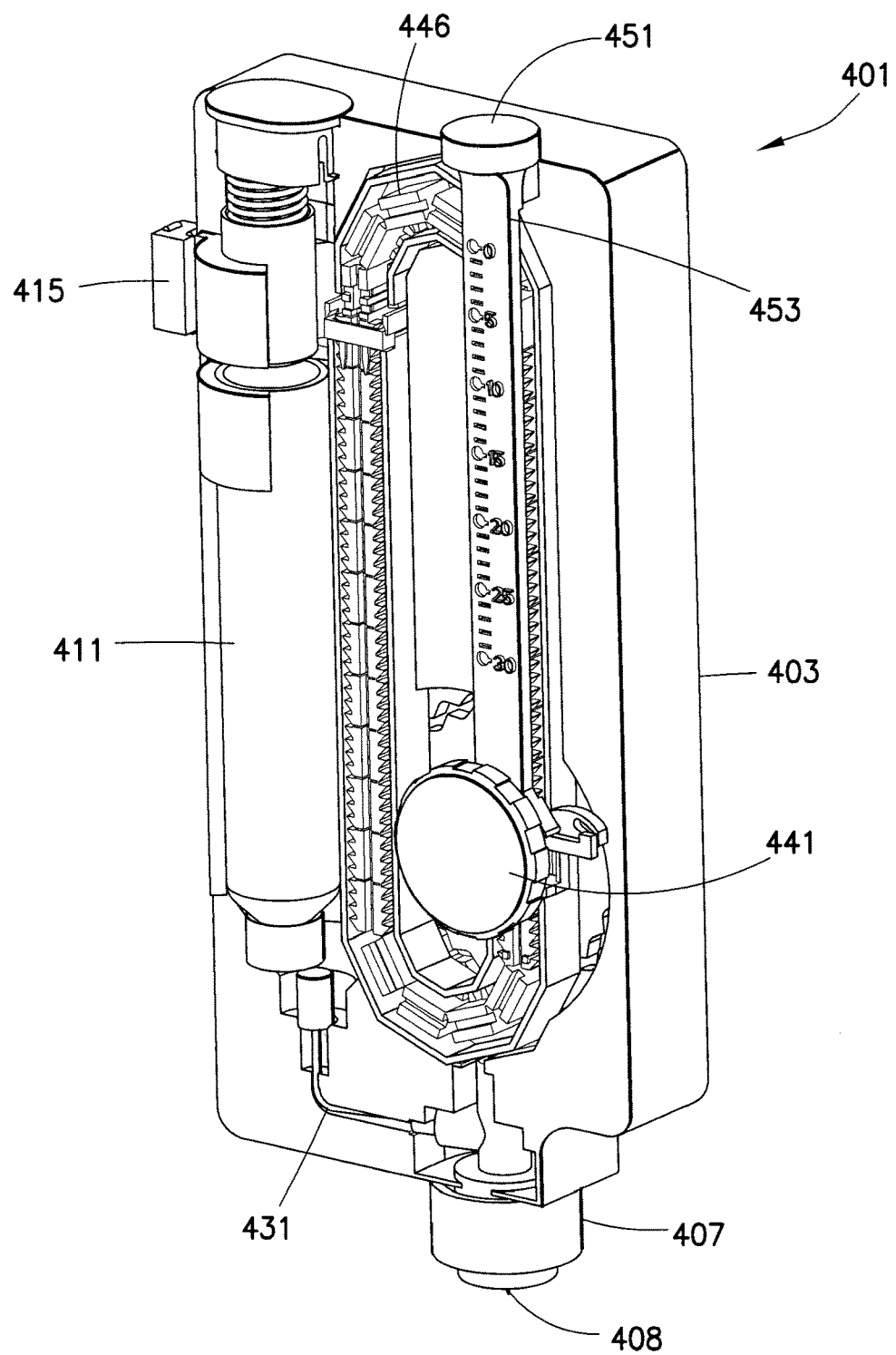
Figure 25:
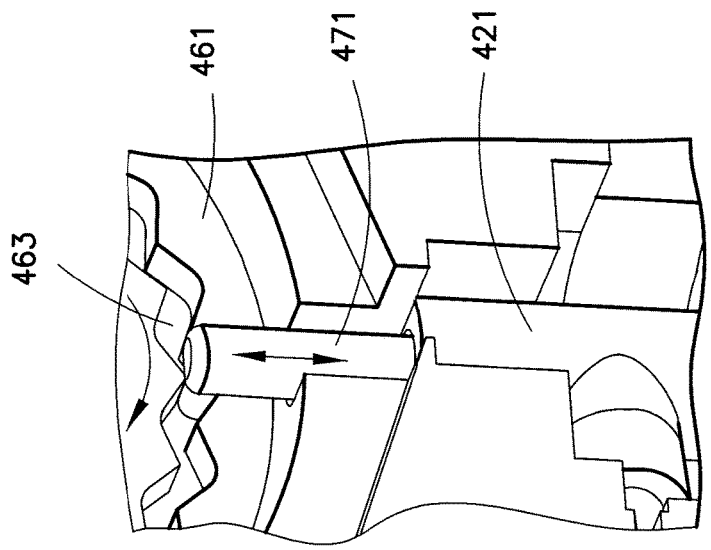
Figure 24:
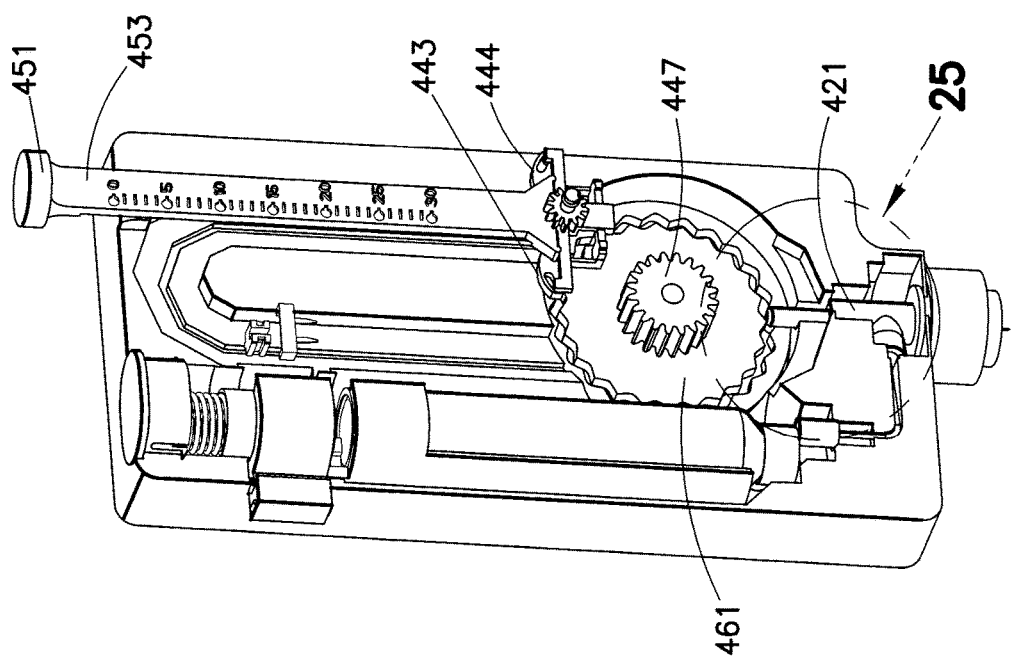

FIGS. 21-25 illustrate the operation of delivering a medicament dose. The inject button 451 is connected to the ratchet 453, and the ratchet teeth 443 and 444 of the ratchet 453 engage the rack teeth 445 such that downward movement of the inject button 451 moves the rack 446 downwardly. The downward movement of the rack 446 (clockwise rotation of the rack 446 as shown in FIG. 21) rotates cam gear 447, which in turn rotates the pump cam 461. The cam gear 447 is fixed to a cam wheel 461, which has a cam groove 463, as shown in FIG. 25. A first end of a cam shaft 465 engages the cam groove 463 and a second end of the cam shaft 465 is connected to a piston 471. As the cam shaft 465 travels along the cam groove 463 the piston is reciprocatingly moved up and down. Rotation of the cam wheel 461 causes reciprocal motion of the piston 471, as shown in FIGS. 24 and 25, thereby delivering the medicament dose in the second chamber 421. During the upstroke of the piston 471, a portion or packet of the medicament dose is drawn from the first chamber 406 to the second chamber 421. During the downstroke of the piston, the medicament dose packet is delivered from the second chamber 421 through the needle 408 and into the skin at the injection site. When the ratchet 451 has been completely reinserted into the housing 403, as shown in FIG. 10, the medicament dose has been fully injected over a sequence of medicament dose packets injected with each downstroke of the piston 471.

Figure 26:
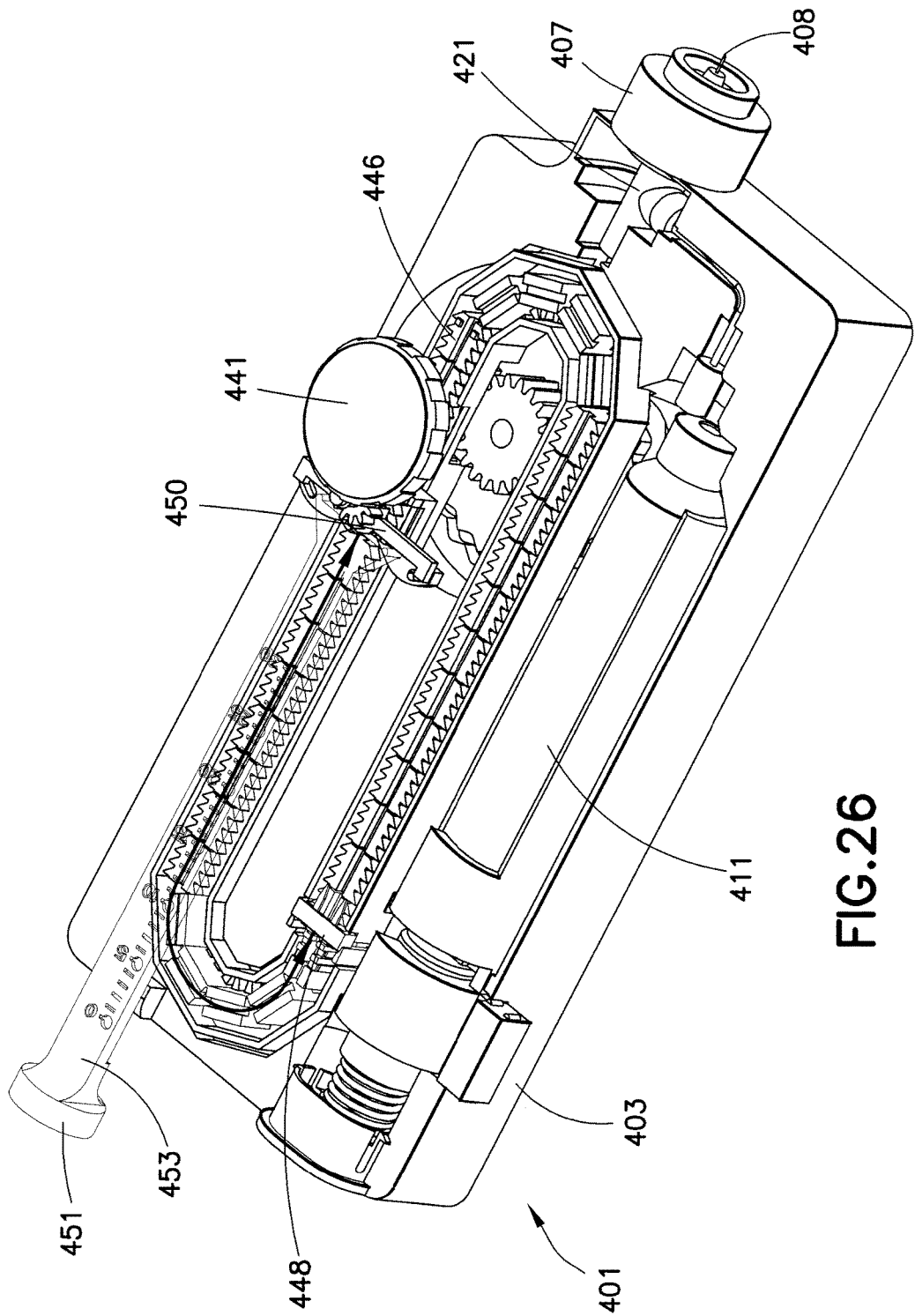

FIGS. 26-34 illustrate the dose tracking operation of the drug delivery device 401. The movable rack 446 has a carriage 448 disposed thereon. As the rack 446 moves, the carriage 448 moves closer to the ratchet teeth 443 and 444, as shown in FIG. 26. Preferably, the rack 446 has a substantially elliptical shape. The ratchet teeth 443 and 444 interfere with the carriage 448 when the first chamber 406 of the cartridge 411 is empty. When the carriage 448 contacts the ratchet teeth 443 and 444 further medicament dose setting is prevented. For example, after approximately 2.5 rack revolutions (cartridge capacity) the carriage 448 prevents further medicament dose setting.

Figures 27B, 27C:
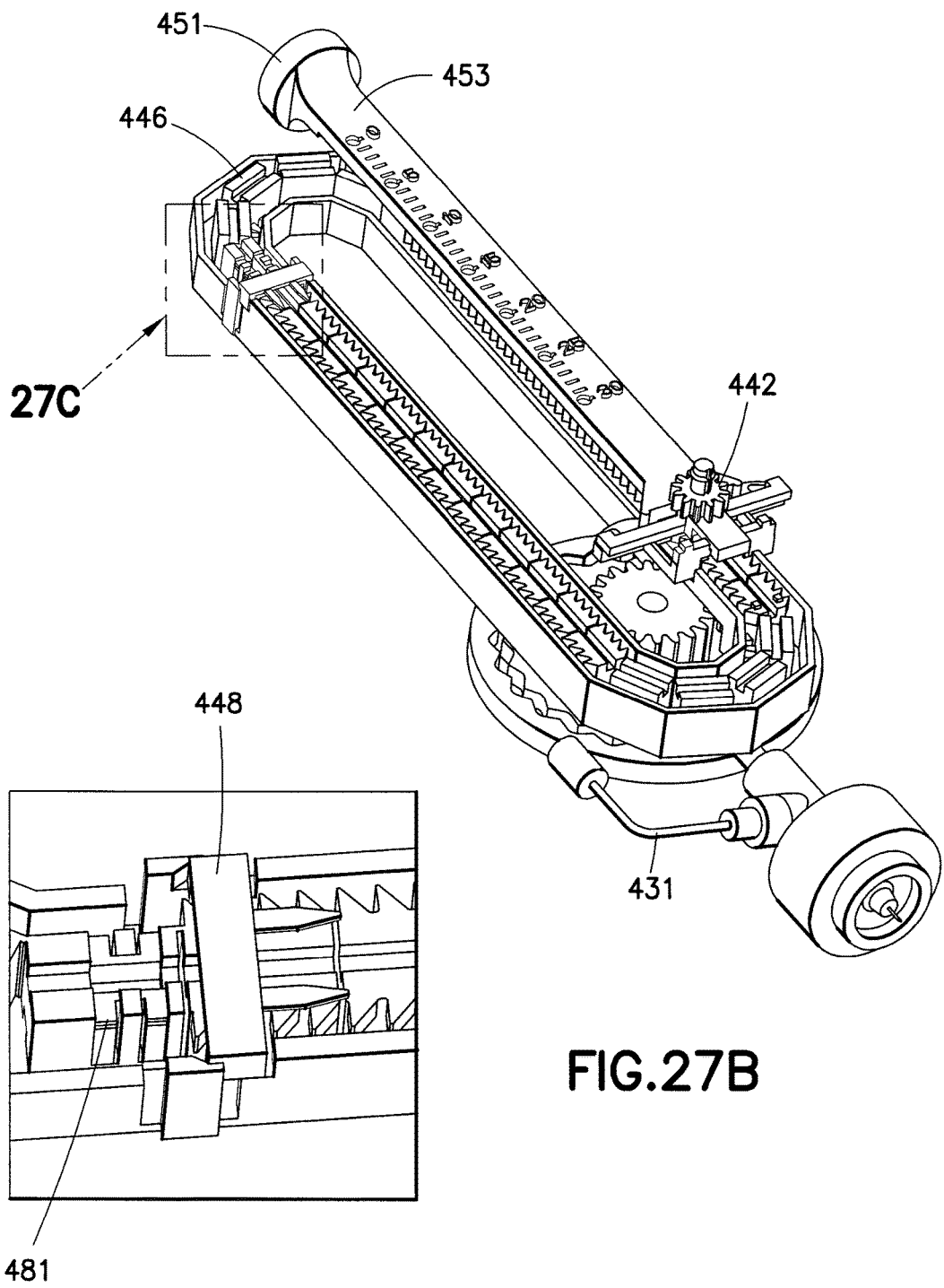
Figure 28A:
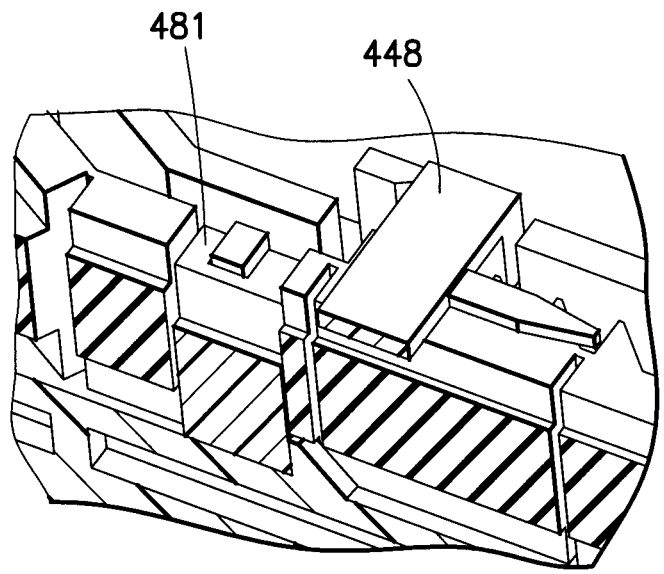
Figure 28B:
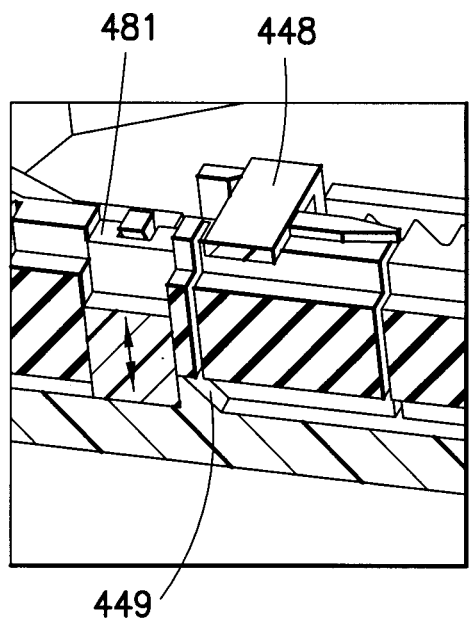
Figure 33:
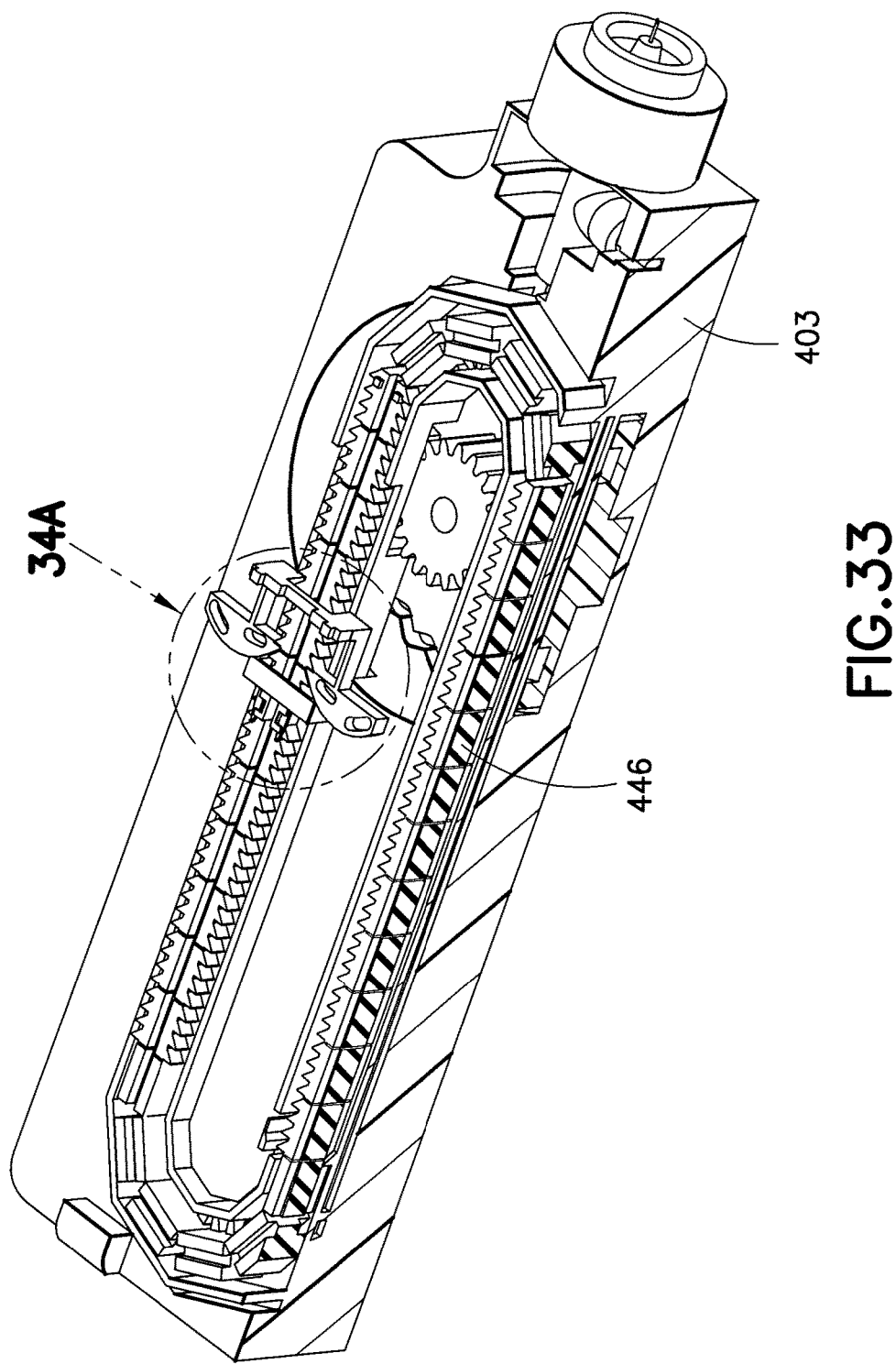
Figure 34A:
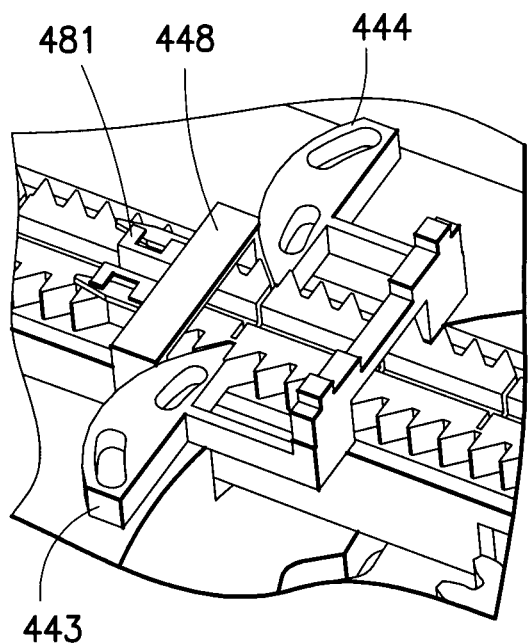
Figure 34B:
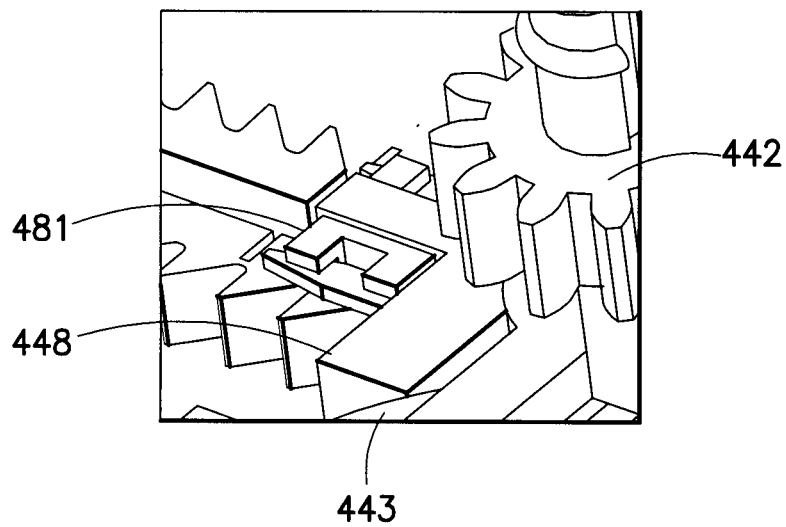

As shown in FIGS. 27 and 28, a medicament dose is ready to be made (the ratchet 453 has been moved outside of the housing 403). When the carriage 448 is in this position, the first chamber 406 is full of medicament. A movable rack member 481 is initially in a first position, as shown in FIGS. 27 and 28, which is a down position and the same position as the remaining members of the rack 446. After the rack 446 makes a first, full revolution, the movable rack member 481 rides up the ramp 449 on the housing 403, as shown in FIGS. 29 and 30. The movable rack member 481 is now in a second, up position, which is above the remaining members of the rack 446. After the rack 446 makes a second, full revolution, the movable rack member 481 engages the carriage 448, as shown in FIGS. 31 and 32. The movable rack member 481 then pushes the carriage 448 with the rack 446 with further movement of the rack 446. After approximately another half revolution, the carriage 448 engages the ratchet teeth 443 and 444, as shown in FIGS. 33 and 34, thereby preventing further dose setting.

Alternatively, the drug delivery device according to exemplary embodiments of the present invention can be used as a reconstituting drug delivery system. The first chamber contains a diluent. The second chamber, which can be removable/replaceable, contains a solid drug. Accordingly, the drug delivery device enables a reconstitution or resuspension system. The first chamber can store sufficient diluent for many injections, and the second chamber can store a solid drug for fewer injections, such as one or two. Accordingly, the drug delivery device according to exemplary embodiments of the present invention can be used as a reconstitution system, including as a reconstitution system for high pressure injections.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A dual-chambered drug delivery device, comprising:
   a cartridge having a first chamber for storing a medicament;
   a second chamber in fluid communication with said first chamber;
   a dose setting member for setting a medicament dose to be injected at an injection site;
   a needle communicating with said second chamber for sequentially injecting portions of the medicament dose into the injection site;
   a ratchet linearly movable between a first ratchet position and a second ratchet position by rotation of said dose setting member, said second ratchet position corresponding to the medicament dose being set; and
   a rack movable by said ratchet when said ratchet is moved from said second ratchet position to said first ratchet position.

2. The dual-chambered drug delivery device according to claim 1, wherein
   upward movement of the dose setting member moves said ratchet upwardly from said first ratchet position to said second ratchet position.

3. The dual-chambered drug delivery device according to claim 1, wherein
   said rack has a movable rack member and a carriage, said movable rack member having a first rack position and a second rack position, said movable rack member moving said carriage when said movable rack member is moving toward said second rack position.

4. The dual-chambered drug delivery device according to claim 3, wherein
   said movable rack member moves up a ramp to move from said first rack position to said second rack position.

5. The dual-chambered drug delivery device according to claim 1, wherein
   said rack is connected to a cam wheel, such that movement of said rack rotates said cam wheel.

6. The dual-chambered drug delivery device according to claim 5, wherein said cam wheel is connected to a piston such that rotation of said cam wheel reciprocatingly moves said piston, an upward stroke of said piston draws a portion of the medicament dose into said second chamber from said first chamber and a downward stroke of said piston expels the portion of the medicament dose.

7. A dual-chambered drug delivery device, comprising:
   a cartridge having a first chamber for storing a medicament;
   a second chamber in fluid communication with said first chamber;
   a dose setting member for setting a medicament dose to be injected at an injection site;

a needle communicating with said second chamber for sequentially injecting portions of the medicament dose into the injection site;

a ratchet movable between a first ratchet position and a second ratchet position by rotation of said dose setting member, said second ratchet position corresponding to the medicament dose being set; and a rack movable by said ratchet when said ratchet is moved from said second ratchet position to said first ratchet position; wherein in said second ratchet position, said ratchet is accessible outside a remaining portion of said dual-chambered drug delivery device.

8. A dual-chambered drug delivery device, comprising:

a cartridge having a first chamber for storing a medicament;

a second chamber in fluid communication with said first chamber;

a dose setting member for setting a medicament dose to be injected at an injection site;

a needle communicating with said second chamber for sequentially infecting portions of the medicament dose into the injection site;

a ratchet movable between a first ratchet position and a second ratchet position by rotation of said dose setting member, said second ratchet position corresponding to the medicament dose being set; and a rack movable by said ratchet when said ratchet is moved from said second ratchet position to said first ratchet position; wherein said rack has a movable rack member and a carriage, said movable rack member having a first rack position and a second rack position, said movable rack member moving said carriage when said movable rack member is moving toward said second rack position; and when said carriage engages teeth connected to said ratchet, further medicament doses are prevented from being set.

9. A dual-chambered drug delivery device, comprising:

a cartridge having a first chamber for storing a medicament;

a second chamber in fluid communication with said first chamber;

a dose setting member for setting a medicament dose to be injected at an injection site;

a needle communicating with said second chamber for sequentially injecting portions of the medicament dose into the injection site;

a ratchet movable between a first ratchet position and a second ratchet position by rotation of said dose setting member, said second ratchet position corresponding to the medicament dose being set; and a rack movable by said ratchet when said ratchet is moved from said second ratchet position to said first ratchet position; wherein said rack has a movable rack member and a carriage, said movable rack member having a first rack position and a second rack position, said movable rack member moving said carriage when said movable rack member is moving toward said second rack position; and said cartridge is pressurized by a compression spring engaging a stopper disposed in said cartridge.

10. The dual-chambered drug delivery device according to claim 9, wherein a force from said compression spring moves said cartridge to pierce a septum of the cartridge.

* * * * *